(12) United States Patent
Fan et al.

(10) Patent No.: US 7,361,488 B2
(45) Date of Patent: *Apr. 22, 2008

(54) NUCLEIC ACID DETECTION METHODS USING UNIVERSAL PRIMING

(75) Inventors: Jian-Bing Fan, San Diego, CA (US); Xiang-Dong Fu, San Diego, CA (US)

(73) Assignees: Illumina, Inc., San Diego, CA (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/215,644

(22) Filed: Aug. 9, 2002

(65) Prior Publication Data

US 2003/0104434 A1 Jun. 5, 2003

Related U.S. Application Data

(63) Continuation-in-part of application No. 09/779,202, filed on Feb. 7, 2001, now Pat. No. 6,812,005, and a continuation-in-part of application No. PCT/US01/04055, filed on Feb. 7, 2001.

(60) Provisional application No. 60/311,194, filed on Aug. 9, 2001, provisional application No. 60/234,731, filed on Sep. 22, 2000, provisional application No. 60/180,810, filed on Feb. 7, 2000.

(51) Int. Cl.
*C12P 19/34* (2006.01)
*C12Q 1/68* (2006.01)
*G01N 33/00* (2006.01)
*C07H 21/02* (2006.01)
*C07H 21/04* (2006.01)

(52) U.S. Cl. .................. 435/91.2; 435/6; 435/91.1; 435/91.51; 436/94; 536/23.1; 536/24.3; 536/24.33

(58) Field of Classification Search ................ 435/6, 435/91.1, 91.2, 91.51, 183, 283.1, 287.1, 435/287.2; 436/94, 501; 536/23.1, 24.3, 536/24.33, 25.3, 25.32

See application file for complete search history.

(56) References Cited

U.S. PATENT DOCUMENTS

| | | | |
|---|---|---|---|
| 4,200,110 A | 4/1980 | Peterson et al. | |
| 4,499,052 A | 2/1985 | Fulwyler | |
| 4,682,895 A | 7/1987 | Costello | |
| 4,785,814 A | 11/1988 | Kane | |
| 4,822,746 A | 4/1989 | Walt | |
| 4,824,789 A | 4/1989 | Yafuso et al. | |
| 4,999,306 A | 3/1991 | Yafuso et al. | |
| 5,002,867 A | 3/1991 | Macevicz | |
| 5,028,545 A | 7/1991 | Soini | |
| 5,105,305 A | 4/1992 | Betzig et al. | |
| 5,114,864 A | 5/1992 | Walt | |
| 5,132,242 A | 7/1992 | Cheung | |
| 5,143,853 A | 9/1992 | Walt | |
| 5,194,300 A | 3/1993 | Cheung | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,302,509 A | 4/1994 | Cheeseman | |
| 5,320,814 A | 6/1994 | Walt et al. | |
| 5,357,590 A | 10/1994 | Auracher | |
| 5,380,489 A | 1/1995 | Sutton et al. | |
| 5,435,724 A | 7/1995 | Goodman et al. | |
| 5,474,895 A | 12/1995 | Ishii et al. | |
| 5,481,629 A | 1/1996 | Tabuchi | |
| 5,494,798 A | 2/1996 | Gerdt et al. | |
| 5,494,810 A | 2/1996 | Barany et al. | |
| 5,496,997 A | 3/1996 | Pope | |
| 5,512,490 A | 4/1996 | Walt et al. | |
| 5,516,635 A | 5/1996 | Ekins et al. | |
| 5,541,311 A | 7/1996 | Dahlberg et al. | |
| 5,554,516 A | 9/1996 | Kacian et al. | |
| 5,565,324 A | 10/1996 | Still et al. | |
| 5,573,909 A | 11/1996 | Singer et al. | |
| 5,575,849 A | 11/1996 | Honda et al. | |
| 5,604,097 A | 2/1997 | Brenner | |
| 5,632,957 A | 5/1997 | Heller et al. | |

(Continued)

FOREIGN PATENT DOCUMENTS

EP 0 269 764 6/1988

(Continued)

OTHER PUBLICATIONS

Boguszewski et al., Cloning of two novel growth hormone transcripts expressed in human placenta. Journal of Clinical Endocrinology and Metabolism, 83, 2878-2885.*
Abel et al., "Fiber-Optic Evanescent Wave Biosensor for the Detection of Oligonucleotides," *Anal. Chem.* 68:2905-2912 (1996).
Nonymous, "Fluorescent Microspheres," Tech. Note 19, Bang Laboratories, (Fishers, In) Feb. 1997.
Anonymous, "Microsphere Selection Guide," Bandg Laboratories, (Fisher, In) Sep. 1998.
Baner et al., "Signal amplification of padlock probes by rolling circle replication," *Nucleic Acids Research*, 26(22): 5073-5078 (1998).
Bangs, L.B., "Immunological Applications of Microspheres," The Latex Course, Bangs Laboratories (Carmel, IN) Apr. 1996.
Barnard et al., "A Fibre-Optic Chemical Sensor with Discrete Sensing Sites," *Nature*, 353:338-340 (Sep. 1991).
Black, "Protein Diversity from Alternative Splicing: A Challenge for Biioninformatics and Post-Genome Biology," *Cell* 103:367-370 (2000).

(Continued)

*Primary Examiner*—Frank Lu
(74) *Attorney, Agent, or Firm*—McDermott Will & Emery LLP

(57) ABSTRACT

The present invention is directed to providing sensitive and accurate assays for gene detection, genome-wide gene expression profiling and alternative splice monitoring with a minimum or absence of target-specific amplification.

14 Claims, 18 Drawing Sheets

U.S. PATENT DOCUMENTS

| | | | |
|---|---|---|---|
| 5,633,972 A | 5/1997 | Walt et al. | |
| 5,639,603 A | 6/1997 | Dower et al. | |
| 5,656,241 A | 8/1997 | Seifert et al. | |
| 5,660,988 A | 8/1997 | Duck et al. | |
| 5,679,524 A | 10/1997 | Nikiforov et al. | |
| 5,690,894 A | 11/1997 | Pinkel et al. | |
| 5,763,175 A | 6/1998 | Brenner | |
| 5,780,231 A | 7/1998 | Brenner | |
| 5,795,714 A | 8/1998 | Cantor et al. | |
| 5,814,524 A | 9/1998 | Walt et al. | |
| 5,830,711 A | 11/1998 | Barany et al. | |
| 5,840,256 A | 11/1998 | Demers et al. | |
| 5,854,033 A | 12/1998 | Lizardi | |
| 5,854,684 A | 12/1998 | Stabile et al. | |
| 5,856,083 A | 1/1999 | Chelsky et al. | |
| 5,858,732 A | 1/1999 | Solomon et al. | |
| 5,863,708 A | 1/1999 | Zanzucchi et al. | |
| 5,888,723 A | 3/1999 | Sutton et al. | |
| 5,900,481 A | 5/1999 | Lough et al. | |
| 5,976,797 A | 11/1999 | Mitsuhashi | |
| 6,013,456 A | 1/2000 | Akgavan-Tafti | |
| 6,023,540 A | 2/2000 | Walt et al. | |
| 6,027,889 A * | 2/2000 | Barany et al. | 435/6 |
| 6,054,564 A | 4/2000 | Barany et al. | |
| 6,096,496 A | 8/2000 | Frankel | |
| 6,110,678 A | 8/2000 | Weisburg et al. | |
| 6,172,218 B1 | 1/2001 | Brenner | |
| 6,251,590 B1 | 6/2001 | Schweighoffer | |
| 6,251,639 B1 | 6/2001 | Kurn | |
| 6,268,148 B1 | 7/2001 | Barany et al. | |
| 6,274,323 B1 | 8/2001 | Bruchez et al. | |
| 6,284,465 B1 | 9/2001 | Wolber | |
| 6,291,166 B1 * | 9/2001 | Gerdes et al. | 435/6 |
| 6,355,431 B1 * | 3/2002 | Chee et al. | 435/6 |
| 6,372,432 B1 | 4/2002 | Tocque et al. | |
| 6,509,153 B1 | 1/2003 | Tocque et al. | |
| 6,713,257 B2 | 3/2004 | Shoemaker | |
| 6,812,005 B2 * | 11/2004 | Fan et al. | 435/91.2 |
| 6,881,571 B1 | 4/2005 | Schweighoffer | |
| 2002/0029113 A1 | 3/2002 | Wang et al. | |
| 2002/0120409 A1 | 8/2002 | Cao et al. | |
| 2003/0087261 A1 | 5/2003 | Bingham | |
| 2003/0100995 A1 | 5/2003 | Loraine et al. | |
| 2004/0009512 A1 | 1/2004 | Ares et al. | |
| 2004/0076959 A1 | 4/2004 | Srinivasan et al. | |
| 2004/0161791 A1 | 8/2004 | Shoemaker | |
| 2005/0214824 A1 | 9/2005 | Balaban | |

FOREIGN PATENT DOCUMENTS

| | | |
|---|---|---|
| EP | 0 392 546 | 10/1990 |
| EP | 0 478 319 | 4/1992 |
| EP | 0 723 146 | 7/1996 |
| WO | WO 89/11101 | 11/1989 |
| WO | WO 93/02360 | 2/1993 |
| WO | WO 93/25563 | 12/1993 |
| WO | WO 94/02515 | 2/1994 |
| WO | WO 95/16918 | 6/1995 |
| WO | WO 95/21271 | 8/1995 |
| WO | WO 96/03212 | 2/1996 |
| WO | WO 96/15271 | 5/1996 |
| WO | WO 96/30392 | 10/1996 |
| WO | WO 97/14028 | 4/1997 |
| WO | WO 97/31256 | 8/1997 |
| WO | WO 97/40385 | 10/1997 |
| WO | WO 97/45559 | 12/1997 |
| WO | WO 97/46704 | 12/1997 |
| WO | WO 98/04746 | 2/1998 |
| WO | WO 98/13523 | 4/1998 |
| WO | WO 98/31836 | 7/1998 |
| WO | WO 98/40726 | 9/1998 |
| WO | WO 98/50782 | 11/1998 |
| WO | WO 98/53093 | 11/1998 |
| WO | WO 98/53300 | 11/1998 |
| WO | WO 99/18434 | 4/1999 |
| WO | WO 99/39001 | 8/1999 |
| WO | WO 99/60170 | 11/1999 |
| WO | WO 99/64867 | 12/1999 |
| WO | WO 99/67414 | 12/1999 |
| WO | WO 99/67641 | 12/1999 |
| WO | WO 00/04372 | 1/2000 |
| WO | WO 00/13004 | 3/2000 |
| WO | WO 00/16101 | 3/2000 |
| WO | WO 00/39587 | 7/2000 |
| WO | WO 00/47996 | 8/2000 |
| WO | WO 00/48000 | 9/2000 |
| WO | WO 00/58516 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/57269 | 8/2001 |

OTHER PUBLICATIONS

Boguszewski et al., "Cloning of Two Novel Growth Hormone Transcripts Expressed in Human Placenta," *J. Clin. Endocrinology and Metabolism*, 83(8):2878-2885 (1998).

Chen et al., "A Microsphere-Based Assay for Multiplexed Single Nucleotide Polymorphism Analysis Using Single Base Chain Extension," *Genome Research*, 10(4):549-557 (2000).

Clark et al., "Genomwide Analysis of mRNA Processing in Yeast Using Splicing-Specific Microarrays," *Science* 296:907-910 (2002).

Czarnik, "Illuminating the SNP Genomic Code," *Modern Drug Discovery*, 1(2): 49-55 (1998).

Drmanac, R. et al., "Sequencing by Hybridization (SBH) with Oligonucleotide Probes as an Integral Approach for the Analysis of Complex Genomes," *International Journal of Genome Research*, 1(1):59-79 (1992).

Drmanac, R. et al., "Sequencing by Hybridization," Automated DNA Sequencing and Analysis, ed. M. Adams, C. Fields and J. Venter. (1994).

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10-13, 1990 Conference at Florida State University. Ed. C. Cantor and H. Lim.

Ferguson et al., "A Fiber-Optic DNA Biosensor Microarray for the Analysis of Gene Expression," *Nature Biotechnology*, 14:1681-1684 (1996).

Fuh et al., "Single Fibre Optic Fluorescence pH Probe," *Analyst*, 112:1159-1163 (1987).

Healey et al., "Development of a Penicillin Biosensor Using a Single Optical Imaging Fiber," *SPIE Proc.* 2388-568-573 (1995).

Healey et al., "Fiberoptic DNA Sensor Array Capable of Detecting Point Mutations," *Analytical Biochemistry*, 251:270-279 (1997).

Healey et al., "Improved Fiber-Optic Chemical Sensor for Penicillin," *Anal. Chem.* 67 (24):4471-4476 (1995).

Herman et al., "Methylation-specific PCR: a novel PCR assay for methylation status of CpG islands," Proc. Natl. Acad. Sci. USA 93:9821-9826 (1996).

Hirschfeld et al., "Laser-Fiber-Optic "Optrode" for Real Time In Vivo Blood Carbon Dioxide Level Monitoring," *J. of Lightwave Technology*, LT-5(7): 1027-1033 (1987).

Hu et al., "Predicting Splice Variant from DNA Chip Expression Data," *Genome Res.* 11:1237-1245 (2001).

Iannone et al., "Multiplexed Single Nucleotide Polymorphism Genotyping by Oligonucleotide Ligation and Flow Cytometry," *Cyometry*, 39:131-140 (2000).

Lizardi et al., "Mutation detection and single-molecule counting using isothermal rolling-circle amplification," *Nature Genetics*, 19:225-232 (Jul. 1998).

Lyamichev et al., "Polymorphism identification and quantitative detection of genomic DNA by invasive cleavage of oligonucleotide probes," *Nature Biotechnology*, 17:292-296 (1999).

Metzker et al., "Termination of DNA synthesis by novel 3'-modified-deoxyribonucleoside 5'- triphosphates," *Nucleic Acids Research*, 22(20):4259-4267 (1994).

Michael et al., "Fabrication of Micro- and Nanostructures Using Optical Imaging Fibers and there Use as Chemical Sensors," Proc. 3rd Intl. Symp., Microstructures and Microfabricated Systems, ed. P. J. Hesketh, et al., v. 97-5, *Electrochem. Soc.*, 152-157 (Aug. 1997).

Michael et al., "Making Sensors out of Disarray: Optical Sensor Microarrays," *Proc. SPIE*, 3270: 34-41 (1998).

Michael et al., "Randomly Ordered Addressable High-Density Optical Sensor Arrays," *Anal. Chem.* 70(7): 1242-1248 (Apr. 1998).

Mignami, et al., "In-Vivo Biomedical Monitoring by Fiber-Optic Systems," *J. of Lightwave Technology*, 13(7): 1396-1406 (1995).

Pantano et al., "Ordered Nanowell Arrays," *Chem. Mater.*, 8(12): 2832-2835 (1996).

Peterson et al., "Fiber-Optic Sensors for Biomedical Applications," *Science*, 13:123-127 (1984).

Peterson, J. et al., "Fiber Optic pH Probe for Physiological Use," *Anal. Chem.*, 52;864-869 (1980).

Piunno et al., "Fiber-Optic DNA Sensor for Fluorometric Nucleic Acid Determination," *Anal. Chem.*, 67:2635-2643 (1995).

Pope, E. "Fiber Optic Chemical Microsensors Employing Optically Active Silica Microspehres," *SPIE*, 2388:245-256 (1995).

Ronaghi et al., "A Sequencing Method Based on Real-Time Pyrophosphate," *Science*, 281:363:365 (1998).

Shoemaker et al., "Quantitative phenotype analysis of yeast deletion mutants using a highly parallel molecular bar-coding strategy," *Nature Genetics*, 14:450-456 (1996).

Shoemaker et al., "Experimental annotation of the human genome using microarray technology," *Nature* 409:922-927 (2001).

Strachan et al., "A Rapid General Method for the Identification of PCR Products Using a Fibre-Optic Biosensor and its Application to the Detection of Listeria," *Letters in Applied Microbiology*, 21:5-9 (1995).

Syvanen, Anne-Christine. "From gels to chips: "Minisequencing" Primer Extension for Analysis of Point Mutations and Single Nucleotide Polymorphisms," *Human Mutation*, 13:1-10 (1999).

Walt, "Fiber-Optic Sensors for Continuous Clinical Monitoring," *Proc. IEEE*, 80(6): 903-911 (1992).

Walt, D. "Fiber Optic Imaging Sensors," *Accounts of Chemical Research*, 31(5):267-278 (1998).

\* cited by examiner

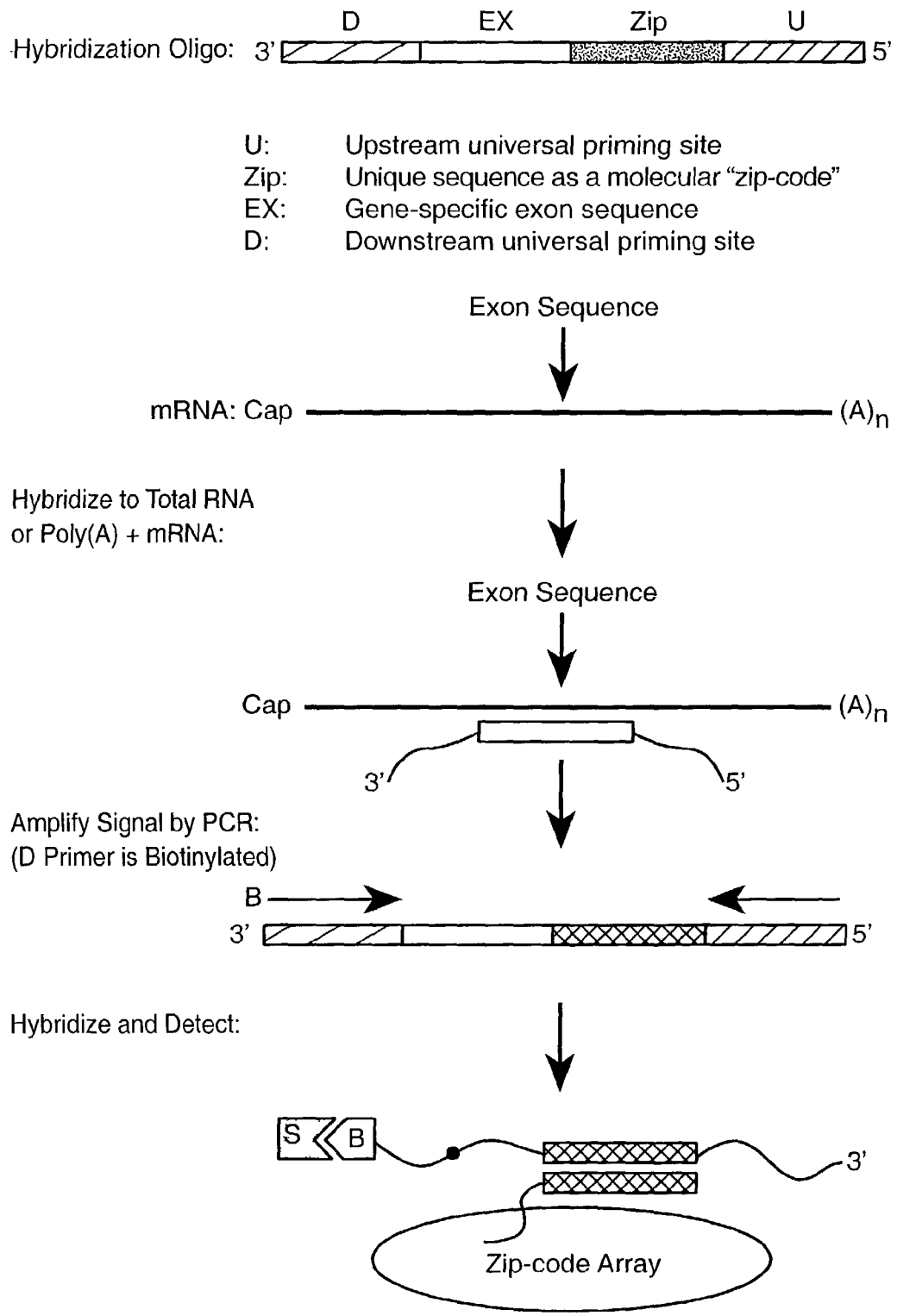
FIG._1

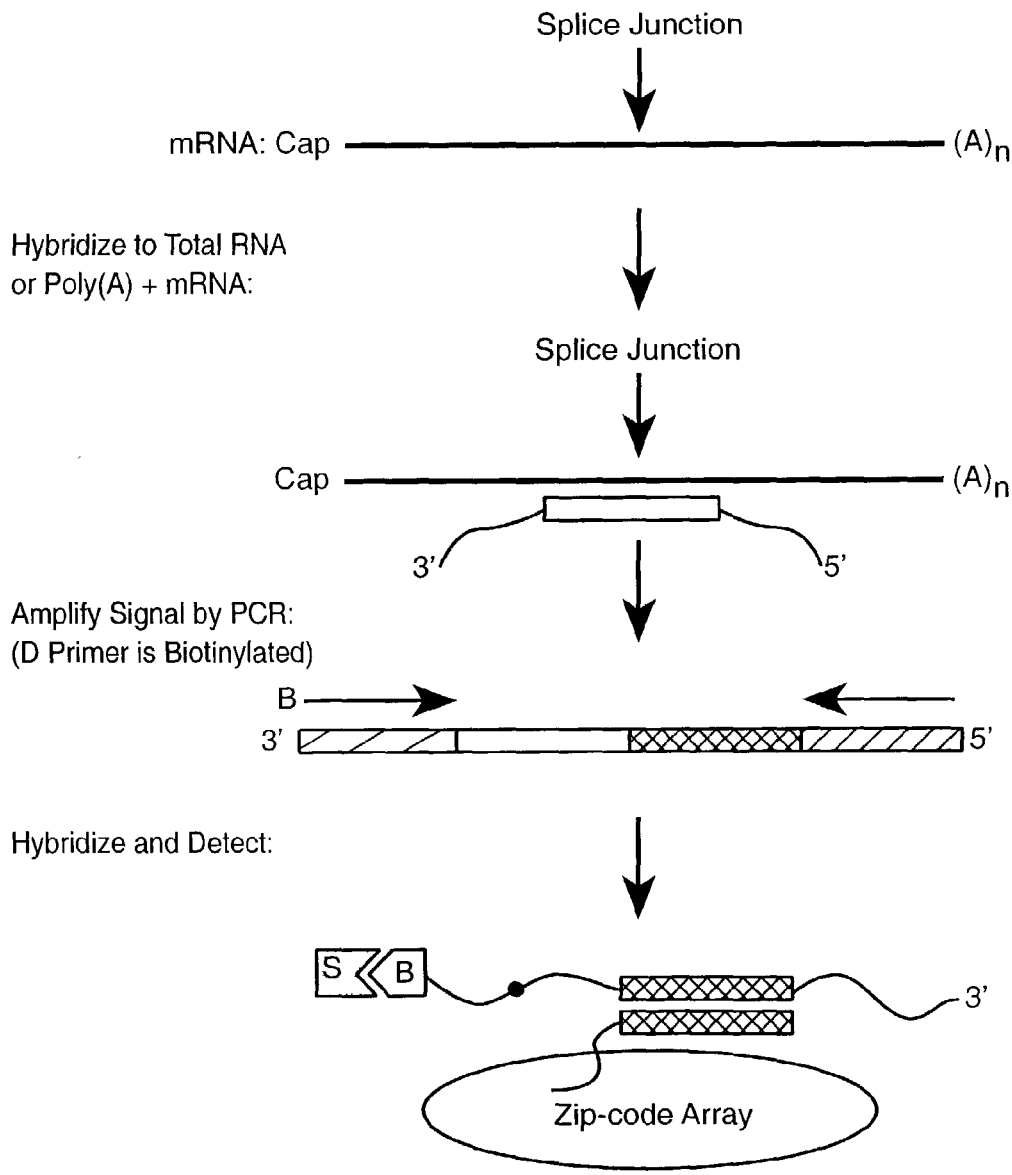
FIG._2

Genome-wide Gene Expression Profiling Using Oligo-ligation Strategy
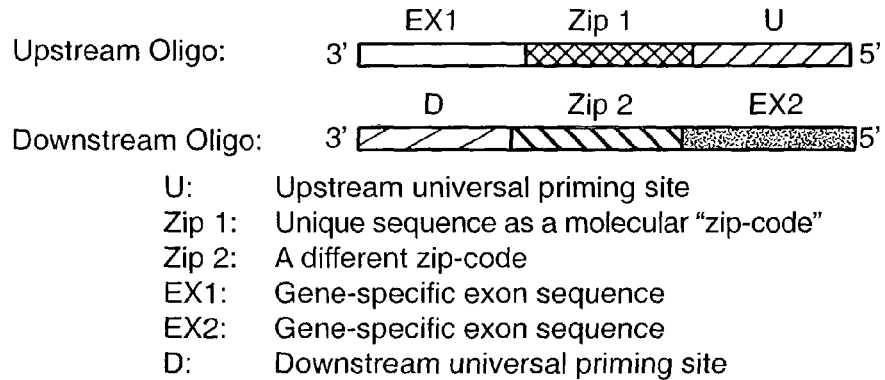
U: Upstream universal priming site
Zip 1: Unique sequence as a molecular "zip-code"
Zip 2: A different zip-code
EX1: Gene-specific exon sequence
EX2: Gene-specific exon sequence
D: Downstream universal priming site
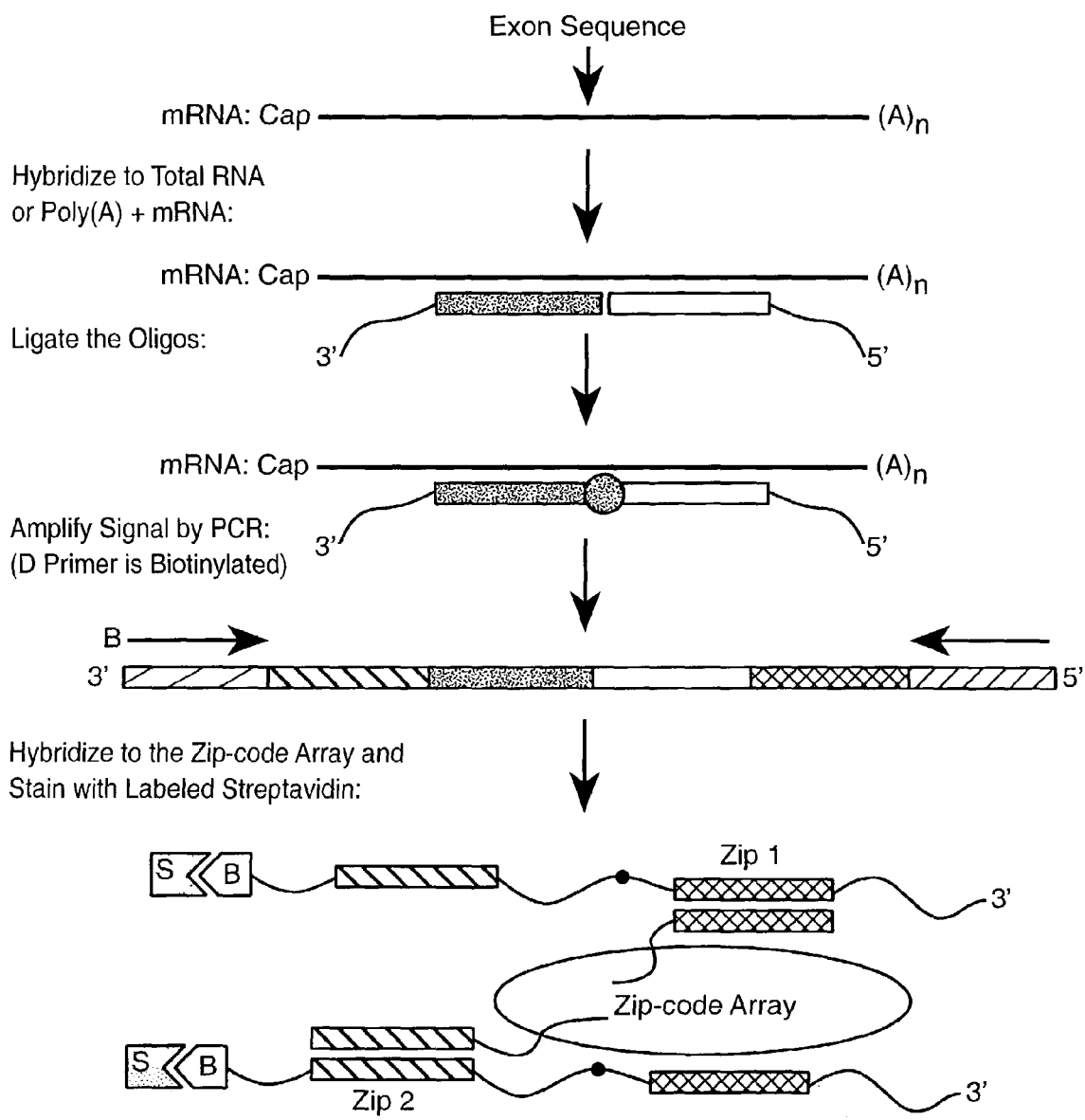
FIG._3

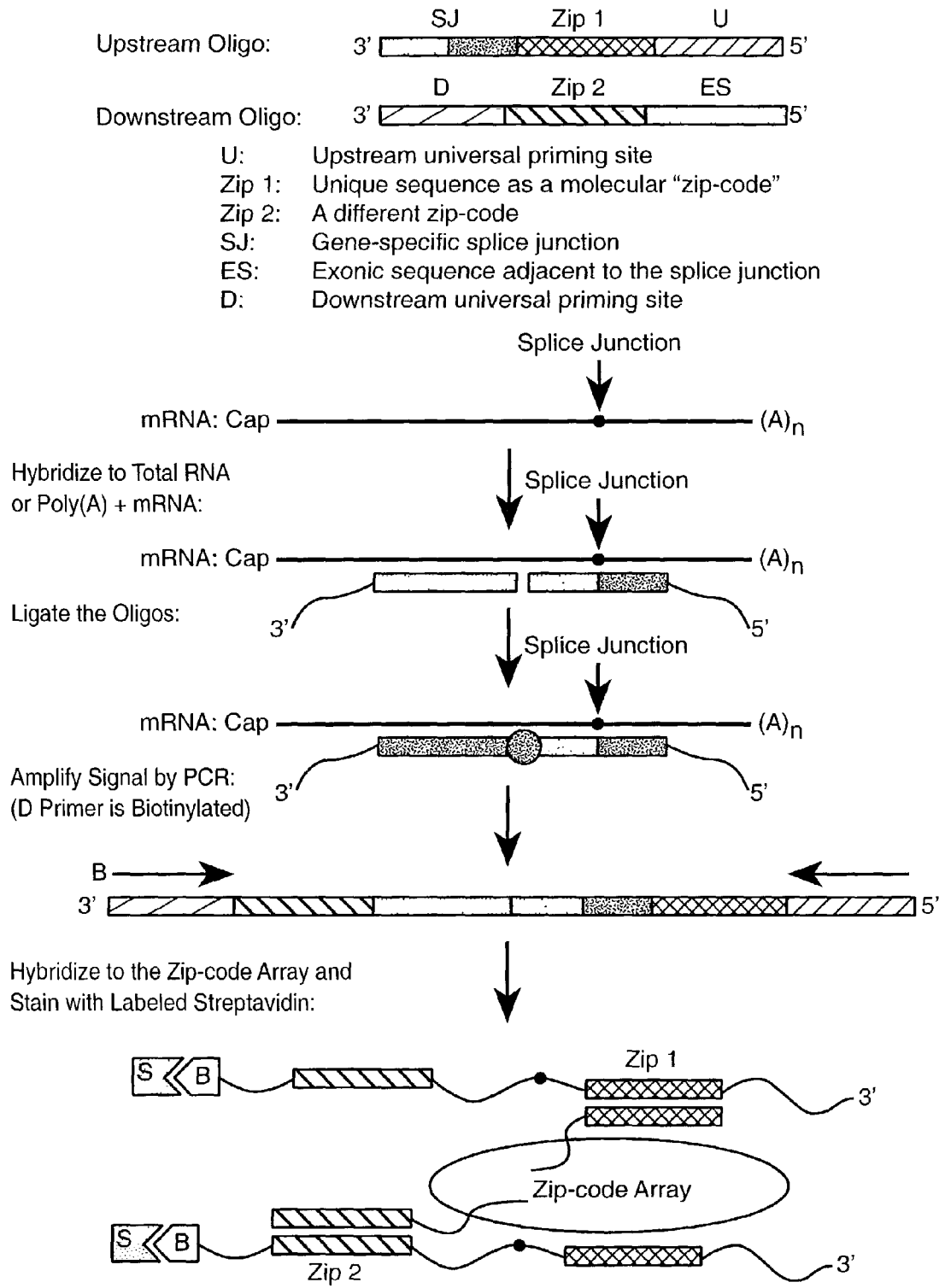
FIG._4

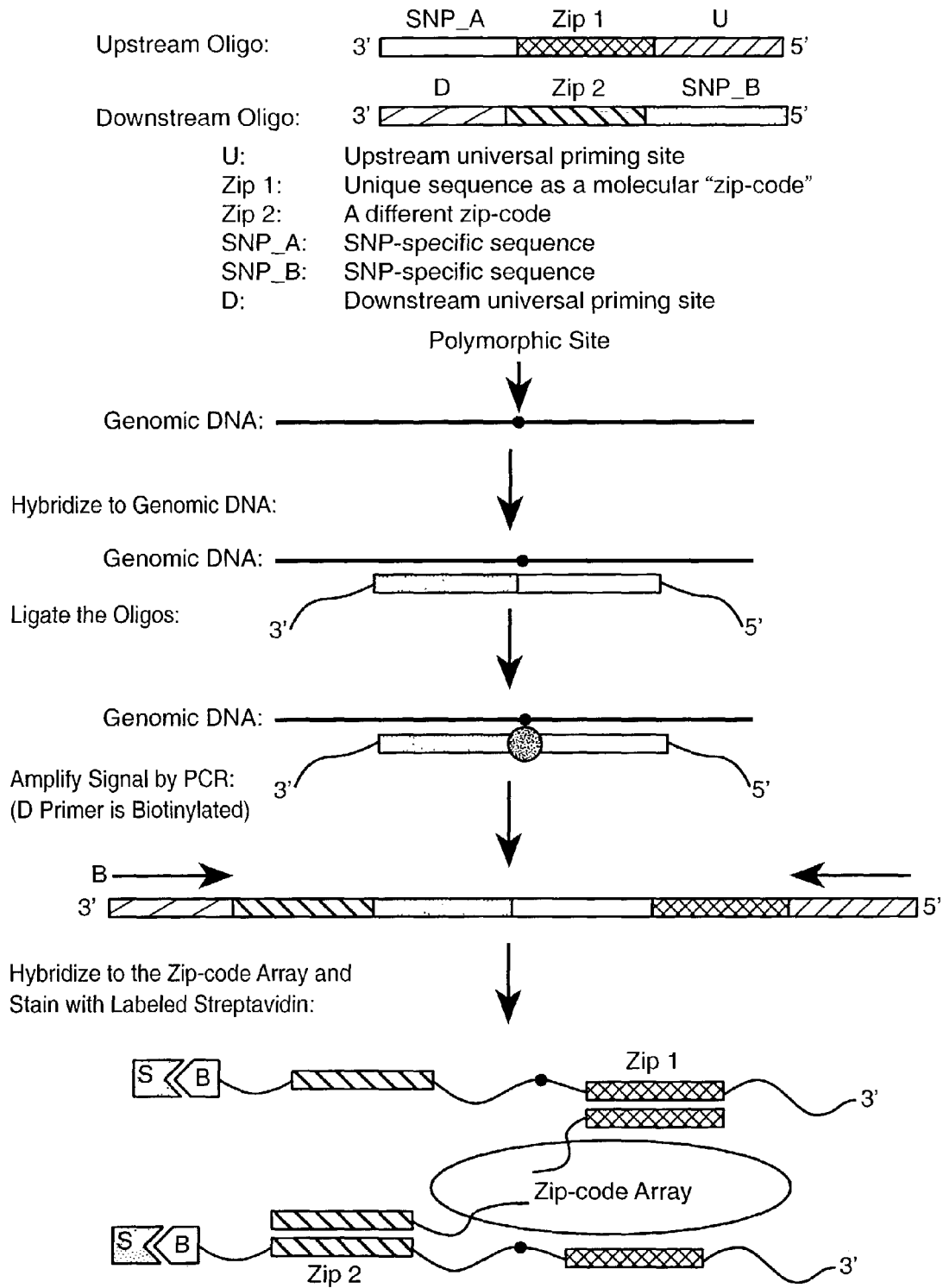
FIG._5

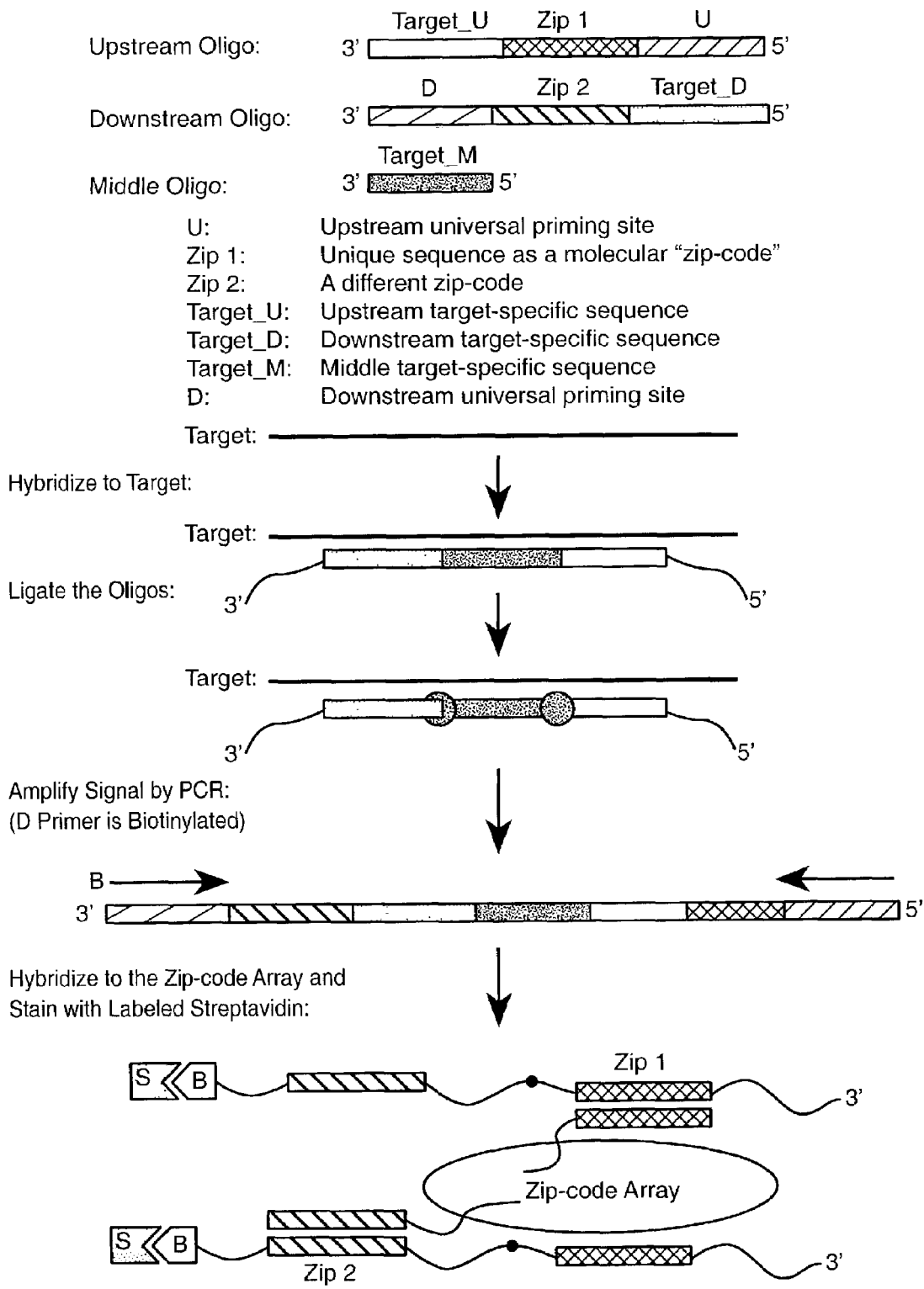
FIG._6

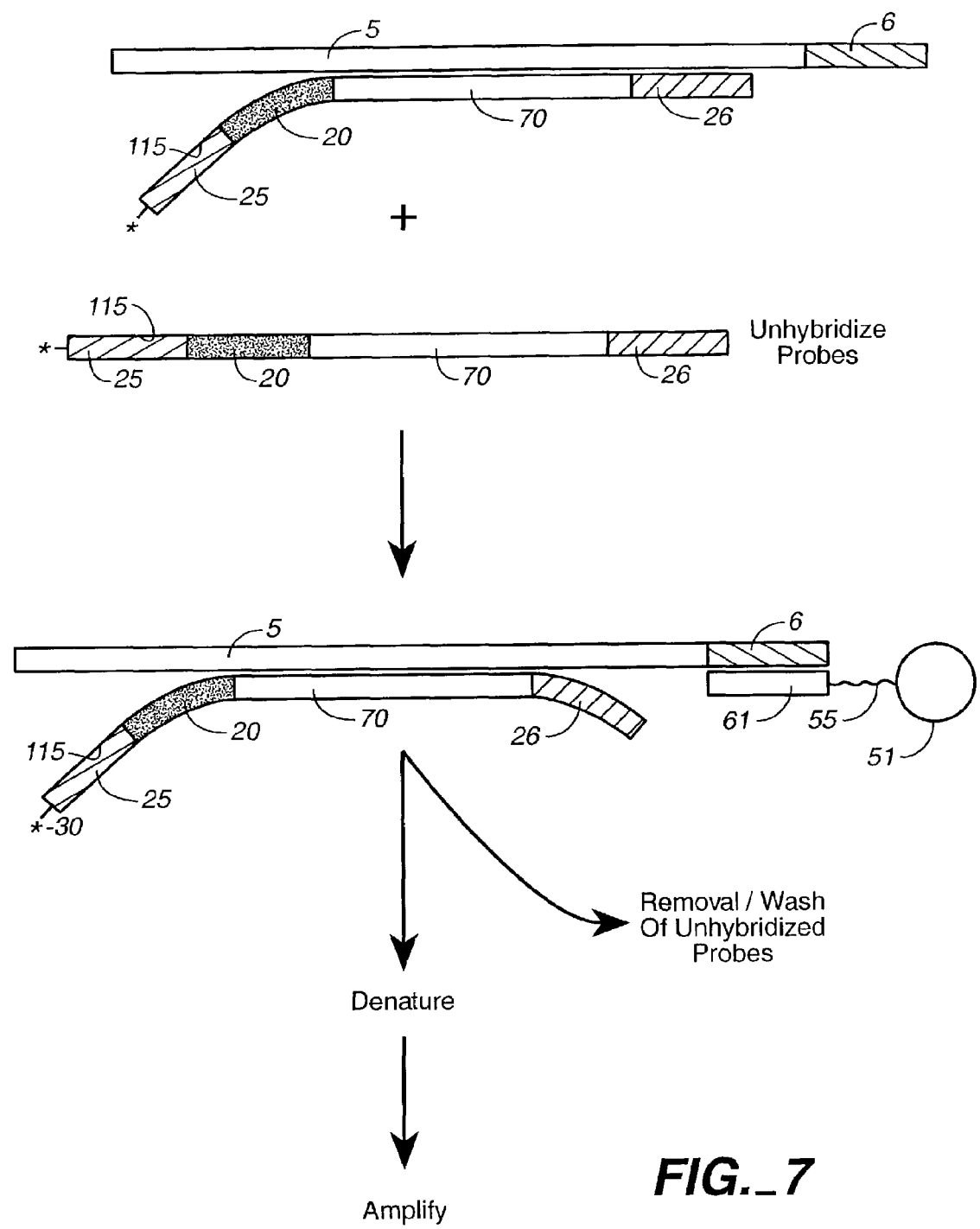
FIG._7

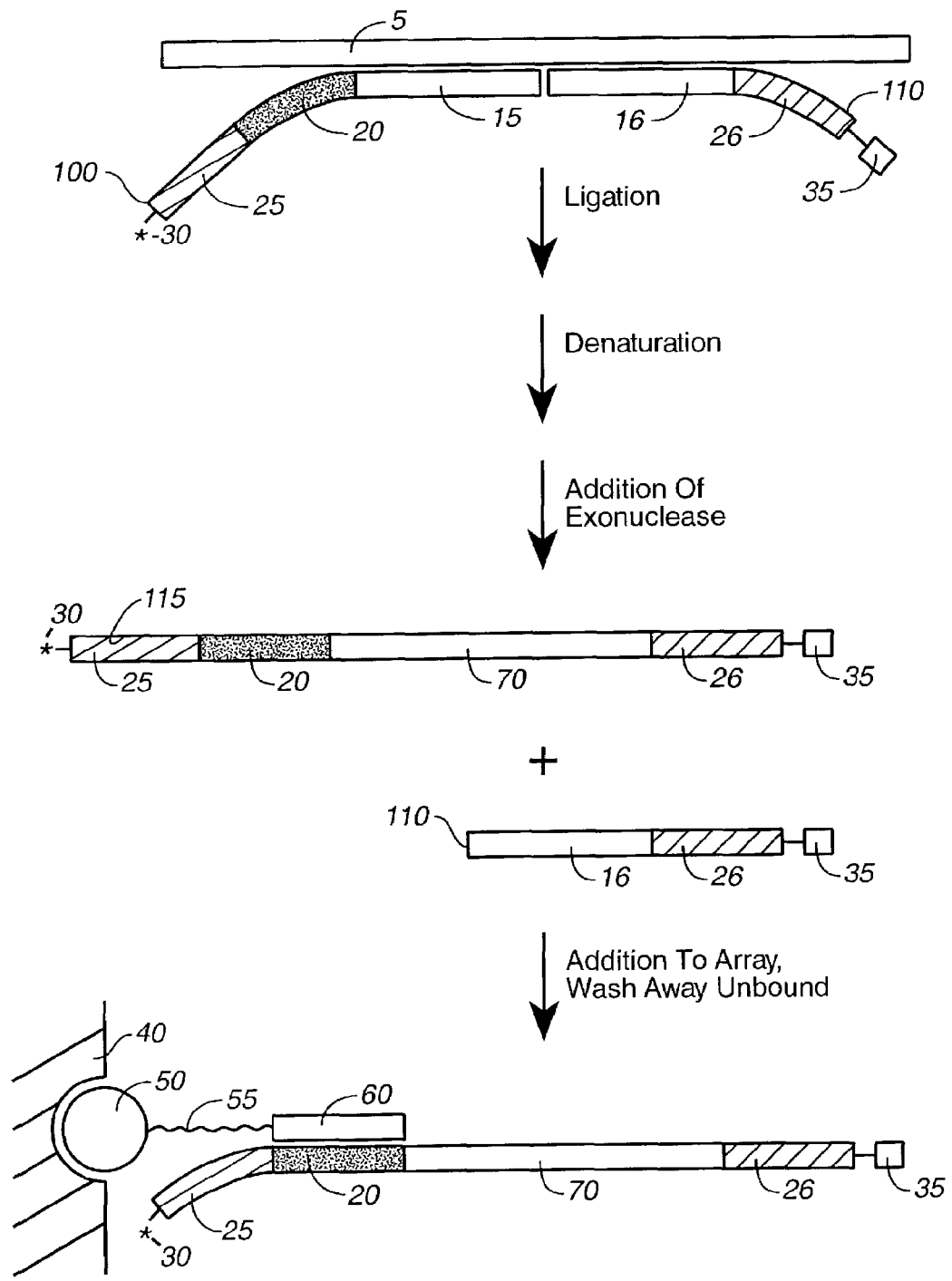
FIG._8

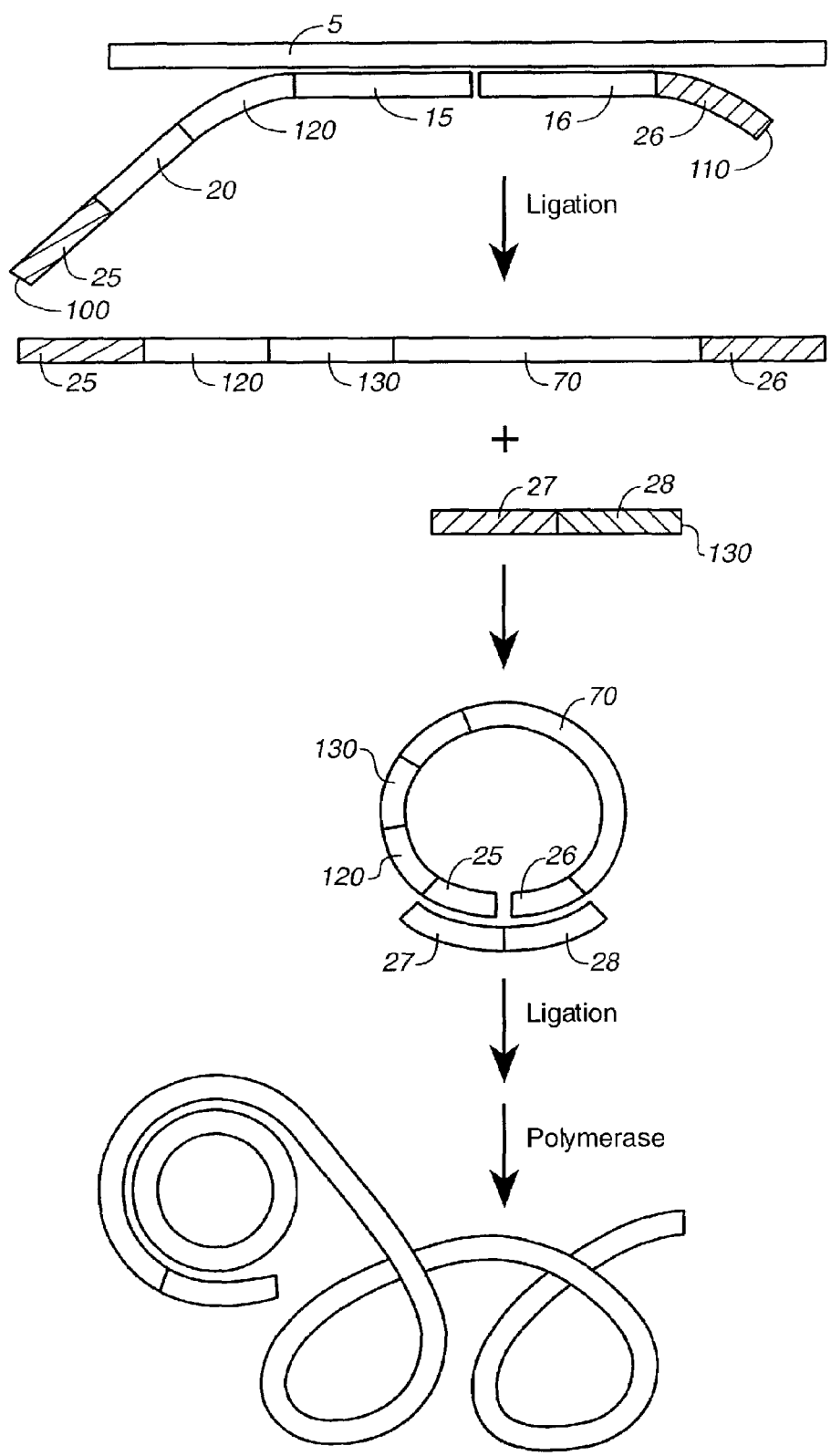
FIG._9

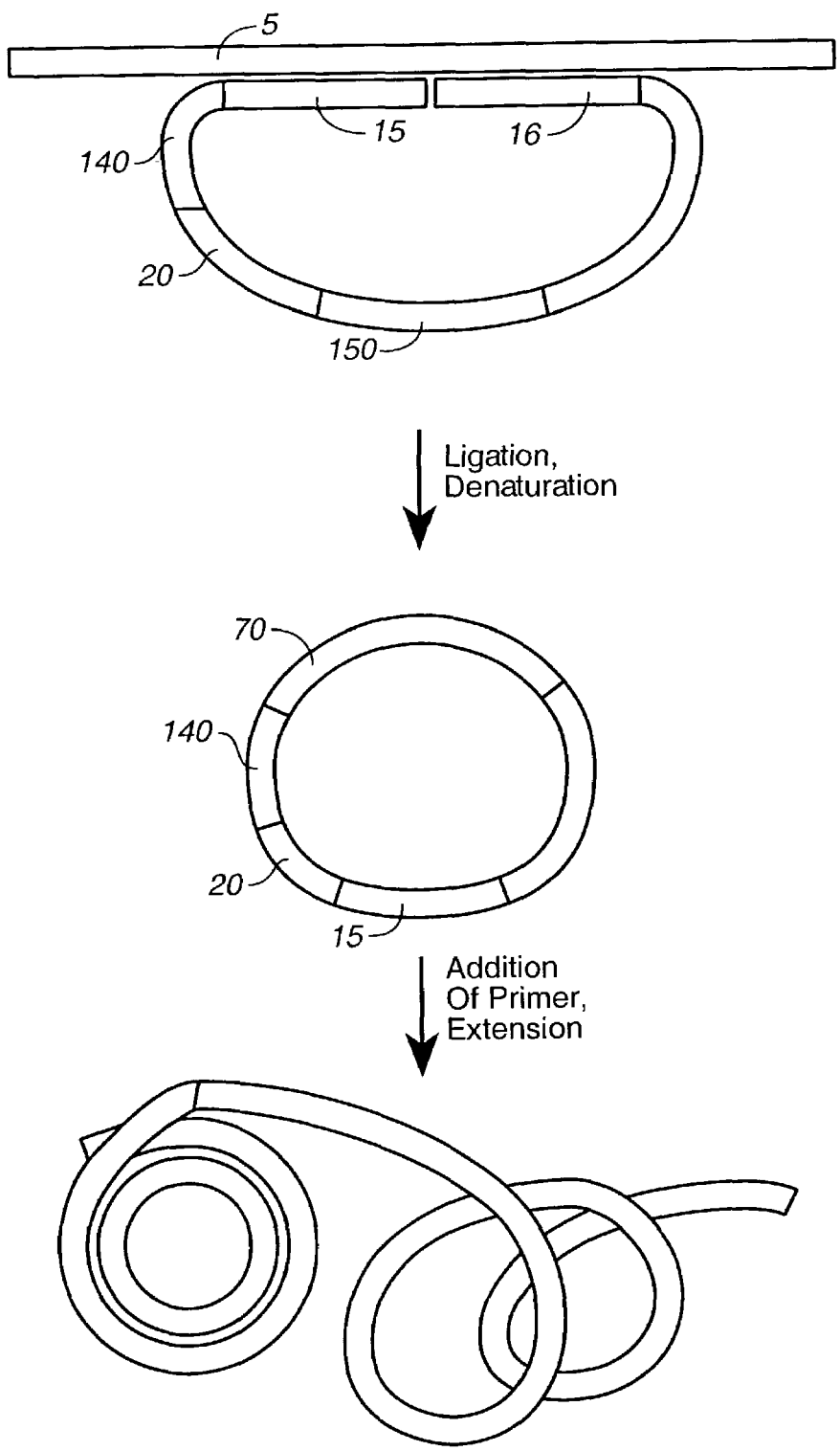
FIG._10

Alternative Splicing Targets Selected for Microarray Analysis

1. GAPDH (constitutive splicing control, signal normalization).

2. FGFR2 / KGF (mutually exclusive exons, internal cell type control):

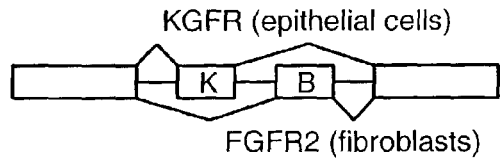

3. Bcl-x (alternative 5' ss):

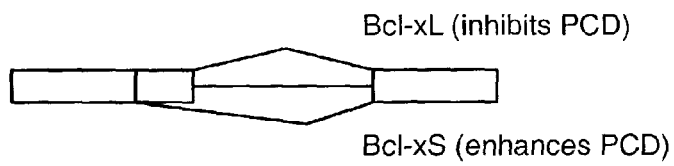

4. c-src (exon inclusion / exclusion):

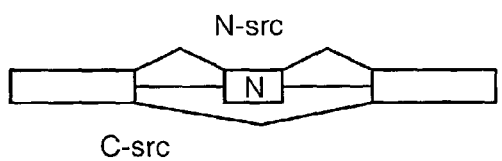

5. CASP2 (exon inclusion / exclusion):

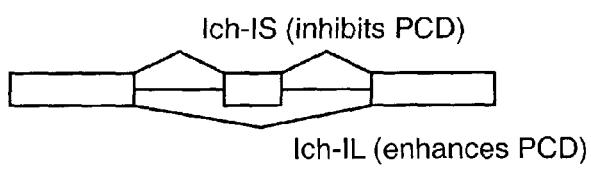

6. CASP9 (alternative 5' ss):

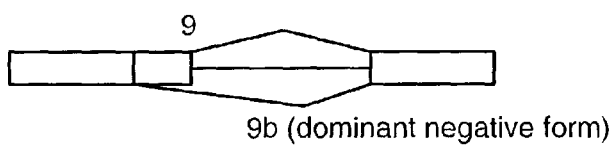

7. Fyn (src family tyrosine kinase, mutually exclusive exons);

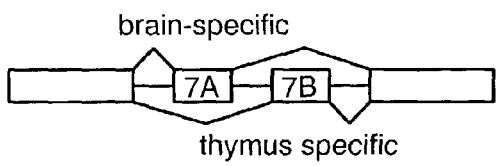

8. NOS1 (alternative promoters / alternative 5' ss):

*FIG._11*

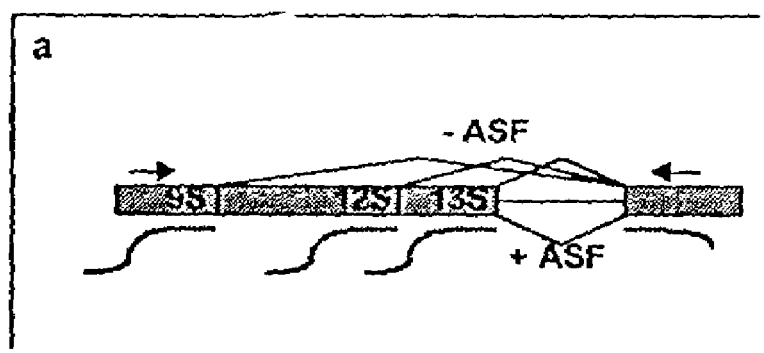
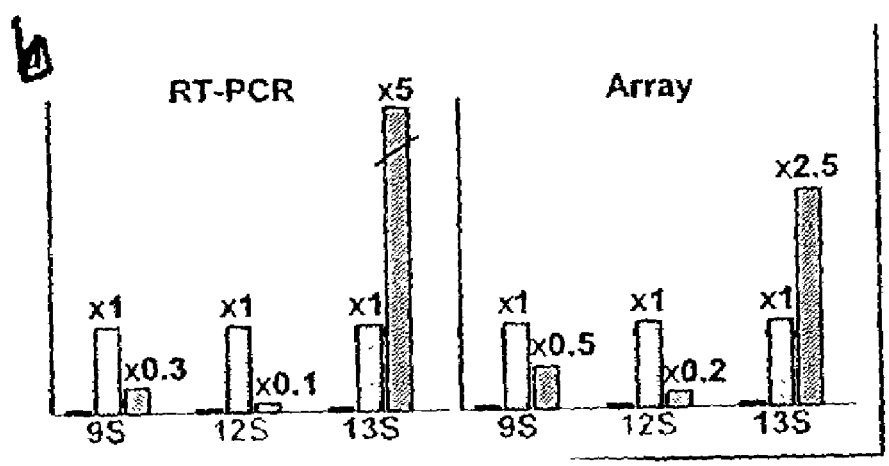
Figure 13 a

293T RNA diluted in HeLa RNA

| | 100fg | 1pg | 10pg | 100pg | 1ng | 10ng | 100ng | 1µg |
|---|---|---|---|---|---|---|---|---|
| 9S | 193 | 170 | 166 | 266 | 214 | 4415 | 2728 | 5163 |
| 12S | 101 | 83 | 350 | 3449 | 8125 | 12507 | 7534 | 7689 |
| 13S | 32 | 53 | 43 | 4751 | 20250 | 32441 | 25057 | 18141 | b

Number of 293T Cells

| | 0 | 1 | 2 | 3 | 4 | 5 | 6 | 8 | 15 | 20 | 35 | 66 |
|---|---|---|---|---|---|---|---|---|---|---|---|---|
| 9S | | | | | | | | | | | | |
| 12S | | | | | | | | | | | | |
| 13S | 14 | 343 | 538 | 615 | 1597 | 1005 | 1434 | 802 | 1035 | 786 | 4018 | 4669 |

Figure 15

NUCLEIC ACID DETECTION METHODS USING UNIVERSAL PRIMING

The present application claims the benefit of applications of U.S. Ser. No. 60/180,810 filed on Feb. 7, 2000, 60/234,731 filed on Sep. 22, 2000, 60/311,194, filed on Aug. 9, 2001, and is a continuation-in-part of Ser. No. 09/779,202, filed on Feb. 7, 2001, now U.S. Pat. No. 6,812,005 B2, and PCT/US01/04055, filed on Feb. 7, 2001, all of which are hereby expressly incorporated by reference.

FIELD OF THE INVENTION

The present invention is directed to providing sensitive and accurate assays for gene detection, genome-wide gene expression profiling and alternative splice monitoring, with a minimum or absence of target-specific amplification.

BACKGROUND OF THE INVENTION

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48-51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41-47 (1993)).

Specificity, in contrast, remains a problem in many currently available gene probe assays. The extent of molecular complementarity between probe and target defines the specificity of the interaction.

Variations in the concentrations of probes, of targets and of salts in the hybridization medium, in the reaction temperature, and in the length of the probe may alter or influence the specificity of the probe/target interaction.

Genes in higher eukaryotes contain introns, which are removed during RNA processing to generate mature functional mRNAs. In most cases, the removal of introns is efficient, and thus these splicing events are constitutive. However, many transcripts are alternatively processed to generate multiple mRNAs from a single mRNA precursor (pre-mRNA) through the use of different 5' or 3' splice sites, exon inclusion or exclusion, and intron retention. The complexity of gene expression is further increased in many cases by coupling alternative splicing with alternative promoters and the use of alternative polyadenylation sites. Based on comparison among expressed sequence tags (ESTs) in databases, it is estimated that as many as 30% of the genes in humans exhibit alternative splicing (Gelfand, M. S., Dubchak, I., Dralyuk, I., & Zorn, M. (1999). ASDB: database of alternatively spliced genes. *Nucleic Acids Research* 27:301-302.). Considering that one transcript often gives rise to more than two isoforms, the number of alternatively spliced mRNAs may surpass the total number of genes that are expressed in a higher eukaryotic organism. Because alternatively spliced transcripts may encode protein isoforms that have distinct functions, it becomes a major challenge in functional genomics to relate a biological function not only to the expression of specific genes but also to their isoforms resulting from post-transcriptional processing. This is particularly relevant to cancer research as molecular alterations during malignancy may result from changes not only in gene expression but also in RNA processing.

The functional consequences of alternative splicing plays a vital role in biology and medicine, with a number of well-known examples being illustrative.

Epithelial cells secrete acidic Fibroblast Growth Factor (aFGF), which binds and activates its receptor FGFR2 on the cell surface of fibroblasts. Conversely, fibroblasts secrete Keratinocyte Growth Factor (KGF), which binds and activates KGFR on epithelial cells. Interestingly, FGFR2 and KGFR are generated from the same pre-mRNA by alternative splicing (Miki T., et al., (1992). Determination of Ligand-binding specificity by alternative splicing: two distinct growth factor receptors encoded by a single gene. *Proc. Natl. Acad. Sci. USA* 89:246-250). Such cell-specific alternative splicing must be tightly regulated because cells expressing both a growth factor and its specific receptor will be transformed to uncontrolled growth.

A number of apoptotic regulators such as Bcl-x, Ced-4, and Caspase-2 (Ich. 1 ) have two isoforms generated by alternative splicing (reviewed by Jiang, Z. H., Zhang, W. J., Rao, Y., & Wu, J. Y. (1998) Regulation of Ich-I pre-mRNA alternative splicing and apoptosis by mammalian splicing factors. *Proc. Natl. Acad. Sci.*, 95:9155-9160). In each case, one form promotes programmed cell death and the other prevents cell death. Thus, alternative splicing provides a life or death choice in determining and regulating the ratio of these isoforms.

CD44 is an important cell surface molecule involved in tissue-specific targeting of T cells, B cells, and macrophages in the immune system as well as in cell adhesion and signal transduction. The transcript has 10 alternative exons, which are included/excluded in combination to generate numerous isoforms. Alterations in CD44 splicing are among the best tumor markers (reviewed by Goodison, S. & Tarin, D. (1998). Current status of CD44 variant isoforms as cancer diagnostic markers. *Histopathology* 32:1-6). CD44 alternative splicing appears to be regulated by cytokines and by oncogenic activation, and the inclusion of a specific exon (v6) was shown to cause tumor metastasis in a model system (Gunthert et al., 1992. A new variant of glycoprotein CD44 confers metastatic potential to rat carcinoma cells. *Cell* 65:13-24).

AML1 is a transcription factor required for granulocyte differentiation. The protein contains an N-terminal DNA binding and protein dimerization domain, and a C-terminal transcriptional activation domain. In 20% of acute myelogenous leukemia (AML) patients, the N-terminal sequence of AML1 is fused to sequences from other chromosomes via chromosome translocation. However, in many AML cases, no chromosome translocation is detected, but a change in alternative splicing of AML1 pre-mRNA appears instead. Alternative splicing results in a truncated version of AML1, which was shown to suppress granulocyte differentiation (Tanaka, T. et al., (1995). An Acute myeloid leukemia gene, AML1, regulates hemopoietic myeloid cell differentiation and transcriptional activation antagonistically by two alternative spliced forms. *EMBO J.* 14:341-350.) Thus, some fraction of AML cases may be triggered by a malfunction in splicing control and regulation.

In conclusion, alternative splicing is associated with important biological events, and in many cases, the pattern or alteration of alternative splicing may be markers for specific diseases and/or targets for disease prevention and intervention.

Alternative RNA splicing is widespread in higher eukaryotic cells and plays a vital role in gene expression. However, detection and analysis of alternative splicing currently rely on RNase protection and RT-PCR assays, which are labor intensive, inefficient, and low scale, especially in the era of functional genomics.

Accordingly, it is an object of the invention to provide a very sensitive and accurate approach for genome-wide gene expression profiling and alternative splice monitoring with a minimum or absence of target-specific amplification.

SUMMARY OF THE INVENTION

In one aspect the invention provides a method of detecting a first target sequence comprising a poly(A) sequence in a sample. The method includes hybridizing a first probe to the target sequence to form a first hybridization complex. The first probe comprises an upstream universal priming site (UUP), an adapter sequence, a first target-specific sequence, and a downstream universal priming site (DUP). The poly(A) sequence remains single-stranded. The method further includes contacting the first hybridization complex with a support comprising a poly(T) sequence, such that the poly(A) sequence hybridizes with the poly(T) sequence. In addition, the method includes removing unhybridized first probe sequences, denaturing the first hybridization complex, amplifying the first probe to generate a plurality of amplicons, contacting the amplicons with an array of capture probes to form assay complexes and detecting the assay complexes.

In addition, the invention provides a method of detecting a first target sequence comprising a first target domain, a second adjacent target domain and a poly(A) sequence. The method includes hybridizing a first probe comprising an upstream universal priming site (UUP) and a first target-specific sequence substantially complementary to the first target domain to the first target domain, and hybridizing a second probe comprising a second target-specific sequence substantially complementary to the second target domain and a downstream universal priming site (DUP), wherein at least one of the first and second probes comprises at least a first adapter sequence. The poly(A) sequence remains single-stranded, and the target sequence and the first and second probes form a ligation complex. The method further includes contacting the ligation complex with a ligase to form a ligated complex, contacting the ligated complex with a support comprising a poly(T) sequence, such that the poly(A) sequence hybridizes with the poly(T) sequence, removing unhybridized first and second probe sequences, denaturing the ligation complex, amplifying the ligated first and second probes to generate a plurality of amplicons, contacting the amplicons with an array of capture probes to form assay complexes, and detecting the assay complexes.

In addition, the invention provides a method of detecting alternative splicing of a first target sequence comprising a poly(A) sequence in a sample comprising contacting the first target sequence with a composition comprising first and second probes. The first and second probes comprising an upstream universal priming site (UUP), an adapter sequence, a first target-specific sequence, wherein said first and second probes comprise a discrete target-specific sequence that is complementary to first and second splice junctions respectively, and a downstream universal priming site (DUP), under conditions whereby the first and second probes hybridize specifically with the first and second splice junctions, to form at least a first hybridization complex, contacting the first hybridization complex with a support comprising a poly(T) sequence, such that the poly(A) sequence hybridizes with the poly(T) sequence, removing unhybridized first probe sequences, denaturing said first hybridization complex, amplifying at least the first probe to generate a plurality of amplicons, contacting the amplicons with an array of capture probes to form assay complexes and detecting the assay complexes as an indication of the presence of the splice junction to thereby detect alternative splicing.

In addition, the invention provides a method of detecting alternative splicing of a first target sequence comprising a first target domain, a second adjacent target domain and a poly(A) sequence. The method includes hybridizing a splice junction specific probe comprising an upstream universal priming site (UUP) at least one adapter and a first target-specific sequence substantially complementary to the first target domain, wherein the first target domain comprises splice junction sequence, to the first target domain, hybridizing a second probe comprising a second target-specific sequence substantially complementary to said second target domain, a downstream universal priming site (DUP), wherein the poly(A) sequence remains single-stranded, and the target sequence and the first or second splice junction specific probe and the second probes form a ligation complex, contacting the ligation complex with a ligase to form a ligated complex, contacting the ligated complex with a support comprising a poly(T) sequence, such that the poly(A) sequence hybridizes with the poly(T) sequence; removing unhybridized probe sequences, denaturing the ligation complex, amplifying the ligated probes to generate a plurality of amplicons, contacting the amplicons with an array of capture probes to form assay complexes and detecting the assay complexes as an indication of the presence of the splice junction sequence, to thereby detect alternative splicing.

BRIEF DESCRIPTION OF THE DRAWINGS

FIG. 1 depicts a flow-chart for array-based detection of gene expression.

FIG. 2 depicts a flow-chart for array-based detection of RNA alternative splicing.

FIG. 3 depicts a flow-chart for genome-wide expression gene expression profiling using oligo-ligation strategy.

FIG. 4 depicts a flow-chart for genome-wide RNA alternative splicing monitoring using oligo-ligation strategy.

FIG. 5 depicts a flow chart for direct genotyping using a whole-genome oligo-ligation strategy.

FIG. 6 depicts a flow-chart of whole-genome oligo-ligation strategy.

FIG. 7 depicts a preferred embodiment of the invention utilizing a poly(A)-poly(T) capture to remove unhybridized probes and targets. Target sequence 5 comprising a poly(A) sequence 6 is hybridized to target probe 115 comprising a target specific sequence 70, an adapter sequence 20, an upstream universal priming site 25, an optional label 30, and a downstream universal priming site 26. The resulting hybridization complex is contacted with a bead 51 comprising a linker 55 and a poly(T) capture probe 61.

FIG. 8 depicts a preferred embodiment of removing non-hybridized target probes, utilizing an OLA format. Target 5 is hybridized to a first ligation probe 100 comprising a first target specific sequence 15, an adapter seqeuence 20, an upstream universal priming site 25, and an optional label 30, and a second ligation probe 110 comprising a second target specific sequence 16, a downstream universal priming site 26, and a nuclease inhibitor 35. After ligation, denaturation of the hybridization complex and addition of an exonuclease, the ligated target probe 115 and the second ligation probe 110 is all that is left. The addition of this to an array (in this embodiment, a bead array comprising substrate 40, bead 50 with linker 55 and capture probe 60 that is substantially complementary to the adapter sequence 20), followed by washing away of the second ligation probe 110 results in a detectable complex.

FIG. 9 depicts a preferred rolling circle embodiment utilizing two ligation probes. Target 5 is hybridized to a first ligation probe 100 comprising a first target specific sequence 15, an adapter seqeuence 20, an unstream universal priming site 25, an adapter sequence 20 and a RCA primer sequence 120, and a second ligation probe 110 comprising a second target specific sequence 16 and a downstream universal priming site 26. Following ligation, an RCA sequence 130 is added, comprising a first universal primer 27 and a second universal primer 28. The priming sites hybridize to the primers and ligation occurs, forming a circular probe. The RCA sequence 130 serves as the RCA primer for subsequent amplification. An optional restriction endonuclease site is not shown.

FIG. 10 depicts preferred a rolling circle embodiment utilizing a single target probe. Target 5 is hybridized to a target probe 115 comprising a first target specific sequence 15, an adapter sequence 20, an upstream universal priming site 25, a RCA priming site 140, optional label sequence 150 and a second target specific sequence 16. Following ligation, denaturation, and the addition of the RCA primer and extension by a polymerase, amplicons are generated. An optional restriction endonuclease site is not shown. 8

FIG. 11 depicts alternative splicing targets selected for microarray analysis. Abbreviations are: GAPGH, D-glyceraldehyde-3-phosphate dehydrogenase glyceraldehyde phosphate dehydrogenase; FGFR2, fibroblast growth factor receptor gene; KGF, keratinocyte growth factor; CASP refers to caspases; NOS, nitric oxide synthase; PCD refers to programmed cell death.

FIG. 13 Demonstrates analysis of E1A alternative splicing by RT-PCR and RASL. a. Diagram of E1A alternative splicing in the absence or presence of the alternative splicing regulator ASF. Each isoform is linked to a unique address sequence. b. Quantitative comparison between RT-PCR and array results.

FIG. 15 Sensitivity of RASL. a. 293T RNA was consecutively diluted into 1 ug of total HeLa RNA followed by analysis by RASL. b. 293T cells present in each well were counted after limited dilution. Cells from representative wells were subjected to direct cell lysis followed by RASL analysis.

DETAILED DESCRIPTION OF THE INVENTION

Figure 12:
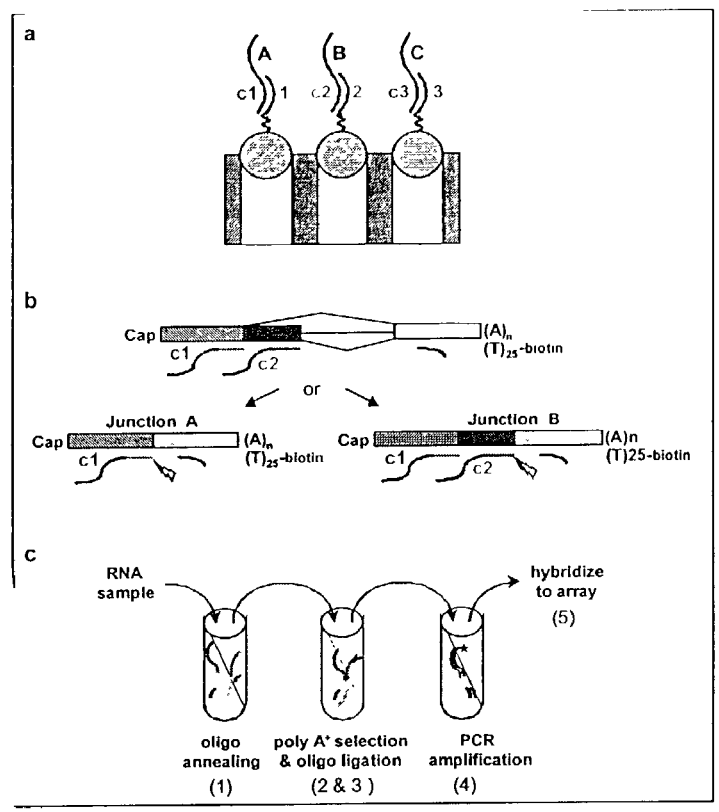
FIG. 12 depicts a schematic of an embodiment of the invention used to identify or detect splice junctions. A. The addressable array. Shown is a section of the array. Beads (three filled circles), each carrying a unique address sequence (1, 2, 3), are embedded on etched optical fibers. Individual targets carrying the sequences (c1, c2, c3) complementary to the addresses can be detected by hybridization. Signals are detected at the opposite ends of the fibers. b. Alternative splicing involving two 5' splice sites competing for a common 3' splice site. Oligos complementary to the 5' splice sites are each linked to an address sequence (c1 or c2). The 5' and 3' oligos also carry primer-landing sequences at their ends. As a result of splicing, distinct oligo partners are established and ligated (lighting symbol). c. The five-step RNA Annealing, Selection, Ligation (RASL) assay. Steps 2 and 3 are carried out in a single streptavidin-coated tube.

The present invention is directed to the detection and quantification of a variety of nucleic acid reactions, particularly using microsphere arrays. In particular, the invention relates to gene detection, gene expression profiling and alternative splice monitoring, without prior amplification of the specific targets. In addition, the invention can be utilized with adapter sequences to create universal arrays.

The invention can be generally described as follows. A plurality of probes (sometimes referred to herein as "target probes") are designed to have at least three different portions: a first portion that is target-specific to an mRNA target and two "universal priming" portions, an upstream and a downstream universal priming sequence. These target probes are hybridized to target mRNA sequences from a sample, without prior amplification, to form hybridization complexes. The hybridization complexes (and non-hybridized target mRNA sequences) are then removed. This is accomplished by using a polyA selection method such as the use of poly(T) sequences on a support that can specifically retain all mRNA including the hybrids. Once the unhybridized target probes are removed, the hybrids are denatured. All the target probes can then be simultaneously amplified using universal primers that will hybridize to the upstream and downstream universal priming sequences. The resulting amplicons, which can be directly or indirectly labeled, can then be detected on arrays, particularly microsphere arrays. This allows the detection and quantification of the mRNA target sequences.

As will be appreciated by those in the art, the system can take on a wide variety of conformations, depending on the assay. For example, when expression profiling or alternate splice junction analysis is to be performed, a single target probe can be used. Thus, a single probe can be designed for any mRNA sequence, with an upstream and downstream universal primer. After separation of the hybridization complexes and amplification, the detection of the mRNA sequence proceeds as outlined below. In the case of splice junction analysis, the target specific portion of the probe has a first domain that hybridizes to the first exon and a second domain that hybridizes to the second exon, and the assay is run under conditions whereby only if both domains hybridize to the target mRNA does the hybridization complex form.

Alternatively, in a preferred embodiment, for example in alternate splice junction analysis, two probes can be used; in this embodiment, the oligonucleotide ligation assay (OLA) can be performed. OLA relies on the fact that two adjacently hybridized probes will be ligated together by a ligase only if there is perfect complementarity at each of the termini, i.e. at a detection position. In this embodiment, there are two ligation probes: a first or upstream ligation probe that comprises the upstream universal priming sequence and a second portion that will hybridize to a first domain of the target mRNA sequence (e.g. the terminus of a first exon, which is therefore a splice junction specific probe), and a second or downstream ligation probe that comprises a portion that will hybridize to a second domain of the target mRNA sequence (e.g. complementary to the terminus of a second exon), adjacent to the first domain, and a second portion comprising the downstream universal priming sequence. If perfect complementarity at the junction exists, the ligation occurs and then the resulting hybridization complex (comprising the mRNA target and the ligated probe) can be separated as above from unreacted probes. Again, the universal priming sites are used to amplify the ligated probe to form a plurality of amplicons that are then detected in a variety of ways, as outlined herein.

In addition, any of the above embodiments can utilize one or more "adapter sequences" (sometimes referred to in the art as "zip codes") to allow the use of "universal arrays". That is, arrays are generated that contain capture probes that are not target specific, but rather specific to individual artificial adapter sequences. One strand of the adapter sequences are added to the target probes (in the case of ligation probes, either probe may contain the adapter sequence), nested between the priming sequences, and thus are included in the amplicons. The adapters are then hybridized to the capture probes on the array, and detection proceeds. In some embodiments, as outlined below, there may be two adapter sequences used in the target probes.

The present invention provides several significant advantages. The method can be used to detect gene expression or alternative splicing events from a single cell or a few cells because of signal amplification of annealed probes. It also allows the direct hybridization of the probes to RNA targets, thus omitting a cDNA conversion step. Additionally, the hybridization reaction occurs in solution rather than on a surface, so that RNA hybridizes more predictably and with favorable kinetics according to their thermodynamic properties. The removal of excess probes and targets allows the isolated targets to reflect the level of individual gene expression level or splicing events in cells and the background signal (due to non-specific interactions) is reduced. Finally, the use of universal primers avoids biased signal amplification in PCR.

Accordingly, the present invention provides compositions and methods for detecting, quantifying and/or identifying specific polyadenylated mRNA nucleic acid sequences in a sample. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred). The sample may comprise individual cells, including primary cells (including bacteria), and cell lines, including, but not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells; osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, 923, HeLa, WI-38, Weri-1, MG-63, etc. See the ATCC cell line catalog, hereby expressly incorporated by reference.

The present invention provides compositions and methods for detecting the presence or absence of target mRNA nucleic acid sequences in a sample. "Target sequence" or grammatical equivalents as used herein means a polyadenylated mRNA sequence or a secondary target such as an amplicon. As is outlined herein, the target sequence may be a polyadenylated mRNA target sequence from a sample, or a secondary target such as an amplicon, which is the product of an amplification reaction such as PCR. Thus, for example, a polyadenylated mRNA target sequence from a sample is amplified to produce an amplicon that is detected. The polyadenylated mRNA target sequence may be any length, with the understanding that longer sequences are more specific. As is outlined more fully below, probes are made to hybridize to polyadenylated mRNA target sequences to determine the presence, absence, quantity or sequence of a polyadenylated mRNA target sequence in a sample. Generally speaking, this term will be understood by those skilled in the art.

The polyadenylated mRNA target sequence may also be comprised of different target domains, that may be adjacent (i.e. contiguous) or separated. For example, in the OLA techniques outlined below, a first ligation probe may hybridize to a first target domain and a second ligation probe may hybridize to a second target domain; either the domains are adjacent, or they may be separated by one or more nucleotides, coupled with the use of a polymerase and dNTPs, as is more fully outlined below. The terms "first" and "second"

are not meant to confer an orientation of the sequences with respect to the 5'-3' orientation of the target mRNA sequence. For example, assuming a 5'-3' orientation of the complementary target sequence, the first target domain may be located either 5' to the second domain, or 3' to the second domain. In addition, as will be appreciated by those in the art, the probes on the surface of the array (e.g. attached to the microspheres) may be attached in either orientation, either such that they have a free 3' end or a free 5' end; in some embodiments, the probes can be attached at one ore more internal positions, or at both ends.

If required, the polyadenylated mRNA target sequence is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

It should be noted that in some cases, two poly(T) steps are used. In one embodiment, a poly(T) support is used to remove unreacted target probes from the sample. However, a poly(T) support may be used to purify or concentrate poly(A) mRNA from a sample prior to running the assay. For example, total RNA may be isolated from a cell population, and then the poly(A) mRNA isolated from the total RNA and fed into the assay systems described below.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95 C., although pH changes and other techniques may also be used.

As outlined herein, the invention provides a number of different nucleic acids primers and probes. By "nucleic acid" or "oligonucleotide" or grammatical equivalents herein means at least two nucleotides covalently linked together. A nucleic acid of the present invention will generally contain phosphodiester bonds, although in some cases, as outlined below, particularly for use with probes, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169-176). Several nucleic acid analogs are described in Rawls, C & E News Jun. 2, 1997 page 35. The nucleic acids can also be "locked nucleic acids". All of these references are hereby expressly incorporated by reference. These modifications of the ribose-phosphate backbone may be done to facilitate the addition of labels, or to increase the stability and half-life of such molecules in physiological environments.

As will be appreciated by those in the art, all of these nucleic acid analogs may find use as probes in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2-4 C drop in Tm for an internal mismatch. With the non-ionic PNA backbone, the drop is closer to 7-9 C. Similarly, due to their non-ionic nature, hybridization of the bases attached to these backbones is relatively insensitive to salt concentration.

The probe nucleic acids may be single stranded or double stranded, as specified, or contain portions of both double stranded or single stranded sequence. Thus, for example, when the target sequence is a polyadenylated mRNA, the hybridization complex comprising the target probe has a double stranded portion, where the target probe is hybridized, and one or more single stranded portions, including the poly(A) portion. The nucleic acid may contain any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No. 5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

Probes and primers of the present invention are designed to have at least a portion be complementary to a polyadenylated mRNA target sequence (either the polyadenylated mRNA target sequence of the sample or to other probe sequences, such as portions of amplicons, as is described below), such that hybridization of the polyadenylated mRNA target sequence and the probes of the present invention occurs. As outlined below, this complementarity need not be perfect; there may be any number of base pair mismatches which will interfere with hybridization between the polyadenylated mRNA target sequence and the single stranded nucleic acids of the present invention. However, if the number of mutations is so great that no hybridization can occur under even the least stringent of hybridization conditions, the sequence is not a complementary polyadenylated mRNA target sequence. Thus, by "substantially complementary" herein is meant that the probes are sufficiently complementary to the polyadenylated mRNA target sequences to hybridize under normal reaction conditions, and preferably give the required specificity.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5-10 C lower than the thermal melting point (Tm) for the specific sequence at a defined ionic strength and pH. The Tm is the temperature (under defined ionic strength, pH and nucleic acid concentration) at which 50% of the probes complementary to the target hybridize to the polyadenylated mRNA target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30 C for short probes (e.g. 10 to 50 nucleotides) and at least about 60 C for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

Thus, the assays are generally run under stringency conditions which allows formation of the first hybridization complex only in the presence of target. Stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The size of the primer and probe nucleic acid may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the universal priming sites of the probes are each preferably about 15-20 nucleotides in length, with 18 being especially preferred. The adapter sequences of the probes are preferably from 15-25 nucleotides in length, with 20 being especially preferred. The target specific portion of the probe is preferably from 15-50 nucleotides in length, with from 30 to 40 being especially preferred.

Accordingly, the present invention provides first target probe sets. By "probe set" herein is meant a plurality of target probes that are used in a particular multiplexed assay. In this context, plurality means at least two, with more 10 than being preferred, depending on the assay, sample and purpose of the test.

Accordingly, the present invention provides first target probe sets that comprise universal priming sites. By "universal priming site" herein is meant a sequence of the probe that will bind a PCR primer for amplification. Each probe preferably comprises an upstream universal priming site (UUP) and a downstream universal priming site (DUP). Again, "upstream" and "downstream" are not meant to convey a particular 5'-3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. In general, universal priming sequences range in size from about 5 to about 35 basepairs, with from about 15 to about 20 being particularly preferred.

As will be appreciated by those in the art, the orientation of the two priming sites is different. That is, one PCR primer will directly hybridize to the first priming site, while the other PCR primer will hybridize to the complement of the second priming site. Stated differently, the first priming site is in sense orientation, and the second priming site is in antisense orientation.

In addition to the universal priming sites, the target probes comprise at least a first target-specific sequence, that is substantially complementary to the polyadenylated mRNA target sequence. As outlined below, ligation probes each comprise a target-specific sequence. As will be appreciated by those in the art, the target-specific sequence may take on a wide variety of formats, depending on the use of probe. For example, for straight polyadenylated-mRNA target sequence detection or gene expression monitoring or profiling, the target-specific probe sequence comprises a portion that will hybridize to all or part of the polyadenylated mRNA target sequence. In addition, a number of particular polyadenylated mRNA target sequences are preferred, including, but not limited to, target sequences that span splice junctions.

In a preferred embodiment, the target specific sequence spans a splice junction of interest. As outlined herein, the target specific sequences are designed to be substantially complementary to sequences at the end of individual alternative exons. By substantially complementary herein is meant that the probes are sufficiently complementary to the target sequences to hybridize under normal reaction conditions, and preferably give the required annealing specificity. Since exons are separated by introns, the detection sequences residue on different parts of the RNA molecule. Thus a target specific sequence is composed of two parts: an upstream portion, complementary to the terminus of a first exon, and a downstream portion, complementary to the terminus of a second exon. Only if splicing has occurred and the intervening intron has been excised will the target specific sequence hybridize to the target sequence under the conditions of the assay.

In another embodiment, two target probes are used to allow the use of OLA assay systems and higher specificity. This may be done to detect any polyadenylated mRNA target sequences, splice junctions, etc., but it finds particular use in the detection of splice junctions.

The basic OLA method can be run at least two different ways; in a first embodiment, only one strand of a target sequence is used as a template for ligation; alternatively, both strands may be used; the latter is generally referred to as Ligation Chain Reaction or LCR. See generally U.S. Pat. Nos. 5,185,243 and 5,573,907; EP 0 320 308 B1; EP 0 336 731 B1; EP 0 439 182 B1; WO 90/01069; WO 89/12696; and WO 89/09835, all of which are incorporated by reference. The discussion below focuses on OLA, but as those in the art will appreciate, this can easily be applied to LCR as well.

In this embodiment, the target probes comprise at least a first ligation probe and a second ligation probe. The method is based on the fact that two probes can be preferentially ligated together, if they are hybridized to a target strand and if perfect complementarity exists at the junction.

In a preferred embodiment, when the assay is done for gene expression purposes (e.g. not splice junction analysis), two ligation probes are designed each with a target specific portion. The first ligation probe is designed to be substantially complementary to a first target domain, and the second ligation probe is substantially complementary to a second target domain. As outlined herein, in a preferred embodiment the first and second target domains are directly adjacent, e.g. they have no intervening nucleotides. In an alternative embodiment, the first and second target domains are indirectly adjacent, e.g. they are intervening nucleotides, and the system includes a polymerase and dNTPs that can be used to "fill in" the gap prior to ligation.

In one embodiment, the target-specific sequences of the first and second ligation probes are designed to span a splice junction. That is, when mRNA is spliced, two exons join together when the intervening intron is spliced out. By having the target probes hybridize "across" the splice junction, or require ligation based on the splice junction, ultimate detection of the splice junction is achieved. Accordingly, in this embodiment, the junction of the probes may be the splice junction itself, or it may be "offset" by one or more nucleotides in either direction.

In this embodiment, at least a first ligation probe is hybridized to the first target domain and a second ligation probe is hybridized to the second target domain. If perfect complementarity exists at the junction, a ligation structure is formed such that the two probes can be ligated together to form a ligated probe. If this complementarity does not exist, no ligation structure is formed and the probes are not ligated together to an appreciable degree. This may be done using heat cycling, to allow the ligated probe to be denatured off the polyadenylated mRNA target sequence such that it may serve as a template for further reactions. In addition, as is more fully outlined below, this method may also be done using three ligation probes or ligation probes that are separated by one or more nucleotides, if dNTPs and a polymerase are added (this is sometimes referred to as "Genetic Bit" analysis).

In general, each target specific sequence of a ligation probe is at least about 5 nucleotides long, with sequences of at from about 15 to 30 being preferred and 20 being especially preferred.

In a preferred embodiment, three or more ligation probes are used. This general idea is depicted in FIG. 6. In this embodiment, there is an intervening ligation probe, specific to a third domain of the target sequence, that is used.

In a preferred embodiment, the two ligation target probes are not directly adjacent. In this embodiment, they may be separated by one or more bases. The addition of dNTPs and a polymerase, as outlined below for the amplification reactions, followed by the ligation reaction, allows the formation of the ligated probe.

In addition to the universal priming sites and the target specific sequence(s), the target probes of the invention further comprise one or more adapter sequences. An "adapter sequence" is a sequence, generally exogenous to the target sequences, e.g. artificial, that is designed to be substantially complementary (and preferably perfectly complementary) to a capture probe on the array. The use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 6 to about 50 basepairs in length, with from about 8 to about 30 being preferred, and from about 15 to about 25 being particularly preferred.

As will be appreciated by those in the art, the placement and orientation of the adapter sequences can vary widely, depending on the configuration of the assay and the assay itself. For example, in most of the OLA embodiments depicted herein, the adapter sequences are shown on the "upstream" ligation probe; however, the downstream probe can also be used. Basically, as will be appreciated by those in the art, the different components of the target probes can be placed in any order, just as long as the universal priming sites remain on the outermost ends of the probe, to allow all sequences between them to be amplified. In general, the adapter sequences will have similar hybridization characteristics, e.g. same or similar melting temperature, similar (G+C) content.

In a preferred embodiment, two adapter sequences per ligated target probe are used. That is, as is generally depicted in FIG. 6, each ligation probe can comprise a different adapter sequence. The ligated probe will then hybridize to two different addresses on the array; this provides a level of quality control and specificity. In addition, it is also possible to use two adapter sequences for single target probes, if desired.

In some embodiments, it is possible to use one or both of the universal primers as an adapter sequence. That is, one of the universal primers can be used to hybridize to a capture probe on the surface. However, in this embodiment, one of the universal primers must be target specific; e.g. one of the universal primers is not really "universal", but rather one primer for each target must allow attachment to a different capture probe.

Thus, the present invention provides target probes that comprise universal priming sequences, target specific sequence(s) and adapter sequences. These target probes are then added to the target sequences to form hybridization complexes. As will be appreciated by those in the art, the hybridization complexes contain portions that are double stranded (the target-specific sequences of the target probes hybridized to a portion of the target mRNA sequence) and portions that are single stranded (the ends of the target probes comprising the universal priming sequences and the adapter sequences, and any unhybridized portion of the target sequence, such as poly(A) tails, as outlined herein).

Preferred assay formats of the present invention are shown in the Figures.

Once the hybridization complexes are formed, unhybridized probes are removed. This is important as all target probes may form some unpredictable structure which will complicate the amplification using the universal priming sequences. Thus to ensure specificity (e.g. that target probes directed to target sequences that are not present in the sample are not amplified and detected), it is important to remove all the nonhybridized probes. The separation of unhybridized target probes is done utilizing supports comprising poly(T) sequences.

Thus, for example, supports (as defined below), particularly magnetic beads, comprising poly(T) sequences are added to the mixture comprising the target sequences and the target probes. In this embodiment, the first hybridization complexes comprise a single-stranded portion comprising a poly(A) sequence, generally ranging from 10 to 100 s adenosines. The poly(T) support is then used to separate the unhybridized target probes from the hybridization complexes. For example, when magnetic beads are used, they may be removed from the mixture and washed; non-magnetic beads may be removed via centrifugation and washed, etc. Alternatively, the poly(T) supports can be packed into a column and the assay mixture run through. In a particularly preferred embodiment, the poly-A sequence is immobilized to the inside of a tube, i.e. a PCR tube, that is coated with poly(T). The hybridization complexes are then released (and denatured) from the beads using a denaturation step such as a thermal step.

Once the non-hybridized probes (and additionally, if preferred, other sequences from the sample that are not of interest) are removed, the hybridization complexes are denatured and the target probes are amplified to form amplicons, which are then detected. This can be done in one of several ways, including PCR amplification and rolling circle amplification. In addition, as outlined below, labels can be incorporated into the amplicons in a variety of ways.

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

In general; PCR may be briefly described as follows. The double stranded hybridization complex is denatured, generally by raising the temperature, and then cooled in the presence of an excess of a PCR primer, which then hybridizes to the first universal priming site. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second universal priming site, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerases include, but are not limited to, the Klenow fragment of DNA polymerase I, SEQUENASE 1.0 and SEQUENASE 2.0 (U.S. Biochemical), T5 DNA polymerase and Phi29 DNA polymerase.

The reaction is initiated by introducing the target probe to a solution comprising the universal primers, a polymerase and a set of nucleotides. By "nucleotide" in this context herein is meant a deoxynucleoside-triphosphate (also called deoxynucleotides or dNTPs, e.g. dATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction requires at least one and preferably two PCR primer, a polymerase, and a set of dNTPs. As outlined herein, the primers may comprise the label, or one or more of the dNTPs may comprise a label.

In a preferred embodiment, the amplification reaction utilizes rolling circle amplification. "Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) *Nuc. Acids Res.* 26:5073-5078; Barany, F. (1991) *Proc. Natl. Acad. Sci. USA* 88:189-193; and Lizardi et al. (1998) *Nat. Genet.* 19:225-232, all of which are incorporated by reference in their entirety.

In general, RCA may be described in two ways, as generally depicted in FIGS. 9 and 10. First, as is outlined in more detail below, a single target probe is hybridized with a target nucleic acid. Each terminus of the probe hybridizes adjacently on the target nucleic acid and the OLA assay as described above occurs. When ligated, the probe is circularized while hybridized to the target nucleic acid. Addition of a polymerase results in extension of the circular probe. However, since the probe has no terminus, the polymerase continues to extend the probe repeatedly. Thus results in amplification of the circular probe.

A second alternative approach involves a two step process. In this embodiment, two ligation probes are initially ligated together, each containing a universal priming sequence. A rolling circle primer is then added, which has portions that will hybridize to the universal priming sequences. The presence of the ligase then causes the original probe to circularize, using the rolling circle primer as the polymerase primer, which is then amplified as above.

These embodiments also have the advantage that unligated probes need not necessarily be removed, as in the absence of the target, no significant amplification will occur. These benefits may be maximized by the design of the probes; for example, in the first embodiment, when there is a single target probe, placing the universal priming site close to the 5' end of the probe since this will only serve to generate short, truncated pieces, without adapters, in the absence of the ligation reaction.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent to the first domain. Hybridization of the oligonucleotide to the target nucleic acid results in the formation of a hybridization complex. Ligation of the "primers" (which are the discrete ends of a single oligonucleotide) results in the formation of a modified hybridization complex containing a circular probe i.e. an RCA template complex. That is, the oligonucleotide is circularized while still hybridized with the target nucleic acid. This serves as a circular template for RCA. Addition of a primer and a polymerase to the RCA template complex results in the formation of an amplicon.

Labeling of the amplicon can be accomplished in a variety of ways; for example, the polymerase may incorporate labelled nucleotides, or alternatively, a label probe is used that is substantially complementary to a portion of the RCA probe and comprises at least one label is used, as is generally outlined herein.

The polymerase can be any polymerase, but is preferably one lacking 3' exonuclease activity (3' exo⁻). Examples of suitable polymerase include but are not limited to exonuclease minus DNA Polymerase I large (Klenow) Fragment, Phi29 DNA polymerase, Taq DNA Polymerase and the like. In addition, in some embodiments, a polymerase that will replicate single-stranded DNA (i.e. without a primer forming a double stranded section) can be used.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labelled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, e.g. is a universal priming site, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

Thus, the padlock probe of the invention contains at each terminus, sequences corresponding to OLA primers. The intervening sequence of the padlock probe contain in no particular order, an adapter sequence and a restriction endonuclease site. In addition, the padlock probe contains a RCA priming site.

Thus, in a preferred embodiment the OLA/RCA is performed in solution followed by restriction endonuclease cleavage of the RCA product. The cleaved product is then applied to an array comprising beads, each bead comprising a probe complementary to the adapter sequence located in the padlock probe. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

In addition, as will be appreciated by those in the art, other amplification reactions may be used; see WO 00/63437, hereby expressly incorporated by reference.

Thus, the present invention provides for the generation of amplicons (sometimes referred to herein as secondary targets).

In a preferred embodiment, the amplicons are labeled with a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair such as biotin/streptavidin; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and a fluorescently labeled streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the amplicon) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less then about $10^{-7}$-$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers as are well known (see 1994 Pierce Chemical Company catalog, technical section on cross-linkers, pages 155-200, incorporated herein by reference).

As outlined herein, labeling can occur in a variety of ways, as will be appreciated by those in the art. In general, labeling can occur in one of two ways: labels are incorporated into primers such that the amplification reaction results in amplicons that comprise the labels or labels are attached to dNTPs and incorporated by the polymerase into the amplicons.

A preferred embodiment utilizes one primer comprising a biotin, that is used to bind a fluorescently labeled streptavidin.

The present invention provides methods and compositions useful in the detection of nucleic acids, particularly the labeled amplicons outlined herein. As is more fully outlined below, preferred systems of the invention work as follows. Amplicons are attached (via hybridization) to an array site. This attachment can be either directly to a capture probe on the surface, through the use of adapters, or indirectly, using capture extender probes as outlined herein. In some embodiments, the target sequence itself comprises the labels. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. In addition, liquid arrays find use in the invention. In this embodiment, microspheres are in solution and analyzed by FACS, as is known in the art. A preferred embodiment utilizes microspheres on a variety of substrates including fiber optic bundles, as are outlined in PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference. While much of the discussion below is directed to the use of microsphere arrays on fiber optic bundles, any array format of nucleic acids on solid supports may be utilized.

Arrays containing from about 2 different bioactive agents (e.g. different beads, when beads are used) to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 m or less (with beads of 200 nm possible) can be used, and very small fibers are known, it is possible to have as many as 40,000 or more (in some instances, 1 million) different elements (e.g. fibers and beads) in a 1 mm$^2$ fiber optic bundle, with densities of greater than 25,000,000 individual beads and fibers (again, in some instances as many as 50-100 million) per 0.5 cm$^2$ obtainable (4 million per square cm for 5 center-to-center and 100 million per square cm for 1 center-to-center).

By "substrate" or "solid support" or other grammatical equivalents herein is meant any material that can be modified to contain discrete individual sites appropriate for the attachment or association of beads and is amenable to at least one detection method. Also, other modifications of the substrate find use in the invention. That is, in some embodiments, the substrate is modified to contain channels or other configurations.

As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates allow optical detection and do not themselves appreciably fluoresce.

Generally the substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. In one embodiment the surface is modified to contain channels into which the microspheres are discributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in U.S. Ser. No. 08/818,199 and U.S. Ser. No. 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are noncovalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with a substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers IN is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

It should be noted that a key component of the invention is the use of a substrate/bead pairing that allows the association or attachment of the beads at discrete sites on the surface of the substrate, such that the beads do not move during the course of the assay.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

Similarly, affinity capture utilizing hybridization can be used to attach nucleic acids to beads.

Alternatively, chemical crosslinking may be done, for example by photoactivated crosslinking of thymidine to reactive groups, as is known in the art.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

When random arrays are used, an encoding/decoding system must be used. For example, when microsphere arrays are used, the beads are generally put onto the substrate randomly; as such there are several ways to correlate the functionality on the bead with its location, including the incorporation of unique optical signatures, generally fluorescent dyes, that could be used to identify the nucleic acid on any particular bead. This allows the synthesis of the capture probes to be divorced from their placement on an array, i.e. the capture probes may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or probe at that particular site can be made.

This means that the beads may be randomly distributed on the array, a fast and inexpensive process as compared to either the in situ synthesis or spotting techniques of the prior art.

However, the drawback to these methods is that for a large array, the system requires a large number of different optical signatures, which may be difficult or time-consuming to utilize. Accordingly, the present invention provides several improvements over these methods, generally directed to methods of coding and decoding the arrays. That is, as will be appreciated by those in the art, the placement of the capture probes is generally random, and thus a coding/decoding system is required to identify the probe at each location in the array. This may be done in a variety of ways, as is more fully outlined below, and generally includes: a) the use a decoding binding ligand (DBL), generally directly labeled, that binds to either the capture probe or to identifier binding ligands (IBLs) attached to the beads; b) positional decoding, for example by either targeting the placement of beads (for example by using photoactivatible or photocleavable moieties to allow the selective addition of beads to particular locations), or by using either sub-bundles or selective loading of the sites, as are more fully outlined below; c) selective decoding, wherein only those beads that bind to a target are decoded; or d) combinations of any of these. In some cases, as is more fully outlined below, this decoding may occur for all the beads, or only for those that bind a particular target sequence. Similarly, this may occur either prior to or after addition of a target sequence. In addition, as outlined herein, the target sequences detected may be either a primary target sequence (e.g. a patient sample), or a reaction product from one of the methods described herein (e.g. an extended SBE probe, a ligated probe, a cleaved signal probe, etc.).

Once the identity (i.e. the actual agent) and location of each microsphere in the array has been fixed, the array is exposed to samples containing the target sequences, although as outlined below, this can be done prior to or during the analysis as well. The target sequences can hybridize (either directly or indirectly) to the capture probes as is more fully outlined below, and results in a change in the optical signal of a particular bead.

In the present invention, "decoding" does not rely on the use of optical signatures, but rather on the use of decoding binding ligands that are added during a decoding step. The decoding binding ligands will bind either to a distinct identifier binding ligand partner that is placed on the beads, or to the capture probe itself. The decoding binding ligands are either directly or indirectly labeled, and thus decoding occurs by detecting the presence of the label. By using pools of decoding binding ligands in a sequential fashion, it is possible to greatly minimize the number of required decoding steps.

In some embodiments, the microspheres may additionally comprise identifier binding ligands for use in certain decoding systems. By "identifier binding ligands" or "IBLs" herein is meant a compound that will specifically bind a corresponding decoder binding ligand (DBL) to facilitate the elucidation of the identity of the capture probe attached to the bead. That is, the IBL and the corresponding DBL form a binding partner pair. By "specifically bind" herein is meant that the IBL binds its DBL with specificity sufficient to differentiate between the corresponding DBL and other DBLs (that is, DBLs for other IBLs), or other components or contaminants of the system. The binding should be sufficient to remain bound under the conditions of the decoding step, including wash steps to remove non-specific binding. In some embodiments, for example when the IBLs and corresponding DBLs are proteins or nucleic acids, the dissociation constants of the IBL to its DBL will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

IBL-DBL binding pairs are known or can be readily found using known techniques. For example, when the IBL is a protein, the DBLs include proteins (particularly including antibodies or fragments thereof (FAbs, etc.)) or small molecules, or vice versa (the IBL is an antibody and the DBL is a protein). Metal ion-metal ion ligands or chelators pairs are also useful. Antigen-antibody pairs, enzymes and substrates or inhibitors, other protein-protein interacting pairs, receptor-ligands, complementary nucleic acids, and carbohydrates and their binding partners are also suitable binding pairs. Nucleic acid—nucleic acid binding proteins pairs are also useful. Similarly, as is generally described in U.S. Pat. Nos. 5,270,163, 5,475,096, 5,567,588, 5,595,877, 5,637, 459, 5,683,867, 5,705,337, and related patents, hereby incorporated by reference, nucleic acid "aptamers" can be developed for binding to virtually any target; such an aptamer-target pair can be used as the IBL-DBL pair. Similarly, there is a wide body of literature relating to the development of binding pairs based on combinatorial chemistry methods.

In a preferred embodiment, the IBL is a molecule whose color or luminescence properties change in the presence of a selectively-binding DBL. For example, the IBL may be a fluorescent pH indicator whose emission intensity changes with pH. Similarly, the IBL may be a fluorescent ion indicator, whose emission properties change with ion concentration.

Alternatively, the IBL is a molecule whose color or luminescence properties change in the presence of various solvents. For example, the IBL may be a fluorescent molecule such as an ethidium salt whose fluorescence intensity increases in hydrophobic environments. Similarly, the IBL may be a derivative of fluorescein whose color changes between aqueous and nonpolar solvents.

In one embodiment, the DBL may be attached to a bead, i.e. a "decoder bead", that may carry a label such as a fluorophore.

In a preferred embodiment, the IBL-DBL pair comprise substantially complementary single-stranded nucleic acids. In this embodiment, the binding ligands can be referred to as "identifier probes" and "decoder probes". Generally, the identifier and decoder probes range from about 4 basepairs in length to about 1000, with from about 6 to about 100 being preferred, and from about 8 to about 40 being particularly preferred. What is important is that the probes are long enough to be specific, i.e. to distinguish between different IBL-DBL pairs, yet short enough to allow both a) dissociation, if necessary, under suitable experimental conditions, and b) efficient hybridization.

In a preferred embodiment, as is more fully outlined below, the IBLs do not bind to DBLs. Rather, the IBLs are used as identifier moieties ("IMs") that are identified directly, for example through the use of mass spectroscopy.

Alternatively, in a preferred embodiment, the IBL and the capture probe are the same moiety; thus, for example, as outlined herein, particularly when no optical signatures are used, the capture probe can serve as both the identifier and the agent. For example, in the case of nucleic acids, the bead-bound probe (which serves as the capture probe) can also bind decoder probes, to identify the sequence of the probe on the bead. Thus, in this embodiment, the DBLs bind to the capture probes.

In a preferred embodiment, the microspheres may contain an optical signature. That is, as outlined in U.S. Ser. Nos. 08/818,199 and 09/151,877, previous work had each subpopulation of microspheres comprising a unique optical signature or optical tag that is used to identify the unique capture probe of that subpopulation of microspheres; that is, decoding utilizes optical properties of the beads such that a bead comprising the unique optical signature may be distinguished from beads at other locations with different optical signatures. Thus the previous work assigned each capture probe a unique optical signature such that any microspheres comprising that capture probe are identifiable on the basis of the signature. These optical signatures comprised dyes, usually chromophores or fluorophores, that were entrapped or attached to the beads themselves. Diversity of optical signatures utilized different fluorochromes, different ratios of mixtures of fluorochromes, and different concentrations (intensities) of fluorochromes.

In a preferred embodiment, the present invention does not rely solely on the use of optical properties to decode the arrays. However, as will be appreciated by those in the art, it is possible in some embodiments to utilize optical signatures as an additional coding method, in conjunction with the present system. Thus, for example, as is more fully outlined below, the size of the array may be effectively increased while using a single set of decoding moieties in several ways, one of which is the use of optical signatures one some beads. Thus, for example, using one "set" of decoding molecules, the use of two populations of beads, one with an optical signature and one without, allows the effective doubling of the array size. The use of multiple optical signatures similarly increases the possible size of the array.

In a preferred embodiment, each subpopulation of beads comprises a plurality of different IBLs. By using a plurality of different IBLs to encode each capture probe, the number of possible unique codes is substantially increased. That is, by using one unique IBL per capture probe, the size of the array will be the number of unique IBLs (assuming no "reuse" occurs, as outlined below). However, by using a plurality of different IBLs per bead, n, the size of the array can be increased to $2^n$, when the presence or absence of each IBL is used as the indicator. For example, the assignment of 10 IBLs per bead generates a 10 bit binary code, where each bit can be designated as "1" (IBL is present) or "0" (IBL is absent). A 10 bit binary code has $2^{10}$ possible variants However, as is more fully discussed below, the size of the array may be further increased if another parameter is included such as concentration or intensity; thus for example, if two different concentrations of the IBL are used, then the array size increases as $3^n$. Thus, in this embodiment, each individual capture probe in the array is assigned a combination of IBLs, which can be added to the beads prior to the addition of the capture probe, after, or during the synthesis of the capture probe, i.e. simultaneous addition of IBLs and capture probe components.

Alternatively, the combination of different IBLs can be used to elucidate the sequence of the nucleic acid. Thus, for example, using two different IBLs (IBL1 and IBL2), the first position of a nucleic acid can be elucidated: for example, adenosine can be represented by the presence of both IBL1 and IBL2; thymidine can be represented by the presence of IBL1 but not IBL2, cytosine can be represented by the presence of IBL2 but not IBL1, and guanosine can be represented by the absence of both. The second position of the nucleic acid can be done in a similar manner using IBL3 and IBL4; thus, the presence of IBL1, IBL2, IBL3 and IBL4 gives a sequence of AA; IBL1, IBL2, and IBL3 shows the sequence AT; IBL1, IBL3 and IBL4 gives the sequence TA, etc. The third position utilizes IBL5 and IBL6, etc. In this way, the use of 20 different identifiers can yield a unique code for every possible 10-mer.

In this way, a sort of "bar code" for each sequence can be constructed; the presence or absence of each distinct IBL will allow the identification of each capture probe.

In addition, the use of different concentrations or densities of IBLs allows a "reuse" of sorts. If, for example, the bead comprising a first agent has a 1× concentration of IBL, and a second bead comprising a second agent has a 10× concentration of IBL, using saturating concentrations of the corresponding labelled DBL allows the user to distinguish between the two beads.

Once the microspheres comprising the capture probes are generated, they are added to the substrate to form an array. It should be noted that while most of the methods described herein add the beads to the substrate prior to the assay, the order of making, using and decoding the array can vary. For example, the array can be made, decoded, and then the assay done. Alternatively, the array can be made, used in an assay, and then decoded; this may find particular use when only a few beads need be decoded. Alternatively, the beads can be added to the assay mixture, i.e. the sample containing the target sequences, prior to the addition of the beads to the substrate; after addition and assay, the array may be decoded. This is particularly preferred when the sample comprising the beads is agitated or mixed; this can increase the amount of target sequence bound to the beads per unit time, and thus (in the case of nucleic acid assays) increase the hybridization kinetics. This may find particular use in cases where the concentration of target sequence in the sample is low; generally, for low concentrations, long binding times must be used.

In general, the methods of making the arrays and of decoding the arrays is done to maximize the number of different candidate agents that can be uniquely encoded. The compositions of the invention may be made in a variety of ways. In general, the arrays are made by adding a solution or slurry comprising the beads to a surface containing the sites for attachment of the beads. This may be done in a variety of buffers, including aqueous and organic solvents, and mixtures. The solvent can evaporate, and excess beads are removed.

In a preferred embodiment, when non-covalent methods are used to associate the beads with the array, a novel method of loading the beads onto the array is used. This method comprises exposing the array to a solution of particles (including microspheres and cells) and then applying energy, e.g. agitating or vibrating the mixture. This results in an array comprising more tightly associated particles, as the agitation is done with sufficient energy to cause weakly-associated beads to fall off (or out, in the case of wells). These sites are then available to bind a different bead. In this way, beads that exhibit a high affinity for the sites are selected. Arrays made in this way have two main advantages as compared to a more static loading: first of all, a higher percentage of the sites can be filled easily, and secondly, the arrays thus loaded show a substantial decrease in bead loss during assays. Thus, in a preferred embodiment, these methods are used to generate arrays that have at least about 50% of the sites filled, with at least about 75% being preferred, and at least about 90% being particularly preferred. Similarly, arrays generated in this manner preferably lose less than about 20% of the beads during an assay, with less than about 10% being preferred and less than about 5% being particularly preferred.

In this embodiment, the substrate comprising the surface with the discrete sites is immersed into a solution comprising the particles (beads, cells, etc.). The surface may comprise wells, as is described herein, or other types of sites on a patterned surface such that there is a differential affinity for the sites. This differnetial affinity results in a competitive process, such that particles that will associate more tightly are selected. Preferably, the entire surface to be "loaded" with beads is in fluid contact with the solution. This solution is generally a slurry ranging from about 10,000:1 beads:solution (vol:vol) to 1:1. Generally, the solution can comprise any number of reagents, including aqueous buffers, organic solvents, salts, other reagent components, etc. In addition, the solution preferably comprises an excess of beads; that is, there are more beads than sites on the array. Preferred embodiments utilize two-fold to billion-fold excess of beads.

The immersion can mimic the assay conditions; for example, if the array is to be "dipped" from above into a microtiter plate comprising samples, this configuration can be repeated for the loading, thus minimizing the beads that are likely to fall out due to gravity.

Once the surface has been immersed, the substrate, the solution, or both are subjected to a competitive process, whereby the particles with lower affinity can be disassociated from the substrate and replaced by particles exhibiting a higher affinity to the site. This competitive process is done by the introduction of energy, in the form of heat, sonication, stirring or mixing, vibrating or agitating the solution or substrate, or both.

A preferred embodiment utilizes agitation or vibration. In general, the amount of manipulation of the substrate is minimized to prevent damage to the array; thus, preferred embodiments utilize the agitation of the solution rather than the array, although either will work. As will be appreciated by those in the art, this agitation can take on any number of forms, with a preferred embodiment utilizing microtiter plates comprising bead solutions being agitated using microtiter plate shakers.

The agitation proceeds for a period of time sufficient to load the array to a desired fill. Depending on the size and concentration of the beads and the size of the array, this time may range from about 1 second to days, with from about 1 minute to about 24 hours being preferred.

It should be noted that not all sites of an array may comprise a bead; that is, there may be some sites on the substrate surface which are empty. In addition, there may be some sites that contain more than one bead, although this is not preferred.

In some embodiments, for example when chemical attachment is done, it is possible to attach the beads in a non-random or ordered way. For example, using photoactivatible attachment linkers or photoactivatible adhesives or masks, selected sites on the array may be sequentially rendered suitable for attachment, such that defined populations of beads are laid down.

The arrays of the present invention are constructed such that information about the identity of the capture probe is built into the array, such that the random deposition of the beads in the fiber wells can be "decoded" to allow identification of the capture probe at all positions. This may be done in a variety of ways, and either before, during or after the use of the array to detect target molecules.

Thus, after the array is made, it is "decoded" in order to identify the location of one or more of the capture probes, i.e. each subpopulation of beads, on the substrate surface.

In a preferred embodiment, pyrosequencing techniques are used to decode the array, as is generally described in "Nucleic Acid Sequencing Using Microsphere Arrays", filed Oct. 22, 1999 (no U.S. Ser. No. received yet), hereby expressly incorporated by reference.

In a preferred embodiment, a selective decoding system is used. In this case, only those microspheres exhibiting a change in the optical signal as a result of the binding of a target sequence are decoded. This is commonly done when the number of "hits", i.e. the number of sites to decode, is generally low. That is, the array is first scanned under experimental conditions in the absence of the target sequences. The sample containing the target sequences is added, and only those locations exhibiting a change in the optical signal are decoded. For example, the beads at either the positive or negative signal locations may be either selectively tagged or released from the array (for example through the use of photocleavable linkers), and subsequently sorted or enriched in a fluorescence-activated cell sorter (FACS). That is, either all the negative beads are released, and then the positive beads are either released or analyzed in situ, or alternatively all the positives are released and analyzed. Alternatively, the labels may comprise halogenated aromatic compounds, and detection of the label is done using for example gas chromatography, chemical tags, isotopic tags mass spectral tags.

As will be appreciated by those in the art, this may also be done in systems where the array is not decoded; i.e. there need not ever be a correlation of bead composition with location. In this embodiment, the beads are loaded on the array, and the assay is run. The "positives", i.e. those beads displaying a change in the optical signal as is more fully outlined below, are then "marked" to distinguish or separate them from the "negative" beads. This can be done in several ways, preferably using fiber optic arrays. In a preferred embodiment, each bead contains a fluorescent dye. After the assay and the identification of the "positives" or "active beads", light is shown down either only the positive fibers or only the negative fibers, generally in the presence of a light-activated reagent (typically dissolved oxygen). In the former case, all the active beads are photobleached. Thus, upon non-selective release of all the beads with subsequent sorting, for example using a fluorescence activated cell sorter (FACS) machine, the non-fluorescent active beads can be sorted from the fluorescent negative beads. Alternatively, when light is shown down the negative fibers, all the negatives are non-fluorescent and the the postives are fluorescent, and sorting can proceed. The characterization of the attached capture probe may be done directly, for example using mass spectroscopy.

Alternatively, the identification may occur through the use of identifier moieties ("IMs"), which are similar to IBLs but need not necessarily bind to DBLs. That is, rather than elucidate the structure of the capture probe directly, the composition of the IMs may serve as the identifier. Thus, for example, a specific combination of IMs can serve to code the bead, and be used to identify the agent on the bead upon release from the bead followed by subsequent analysis, for example using a gas chromatograph or mass spectroscope.

Alternatively, rather than having each bead contain a fluorescent dye, each bead comprises a non-fluorescent precursor to a fluorescent dye. For example, using photocleavable protecting groups, such as certain ortho-nitrobenzyl groups, on a fluorescent molecule, photoactivation of the fluorochrome can be done. After the assay, light is shown down again either the "positive" or the "negative" fibers, to distinguish these populations. The illuminated precursors are then chemically converted to a fluorescent dye. All the beads are then released from the array, with sorting, to form populations of fluorescent and non-fluorescent beads (either the positives and the negatives or vice versa).

In an alternate preferred embodiment, the sites of attachment of the beads (for example the wells) include a photopolymerizable reagent, or the photopolymerizable agent is added to the assembled array. After the test assay is run, light is shown down again either the "positive" or the "negative" fibers, to distinguish these populations. As a result of the irradiation, either all the positives or all the negatives are polymerized and trapped or bound to the sites, while the other population of beads can be released from the array.

In a preferred embodiment, the location of every capture probe is determined using decoder binding ligands (DBLs). As outlined above, DBLs are binding ligands that will either bind to identifier binding ligands, if present, or to the capture probes themselves, preferably when the capture probe is a nucleic acid or protein.

In a preferred embodiment, as outlined above, the DBL binds to the IBL.

In a preferred embodiment, the capture probes are single-stranded nucleic acids and the DBL is a substantially complementary single-stranded nucleic acid that binds (hybridizes) to the capture probe, termed a decoder probe herein. A decoder probe that is substantially complementary to each candidate probe is made and used to decode the array. In this embodiment, the candidate probes and the decoder probes should be of sufficient length (and the decoding step run under suitable conditions) to allow specificity; i.e. each candidate probe binds to its corresponding decoder probe with sufficient specificity to allow the distinction of each candidate probe.

In a preferred embodiment, the DBLs are either directly or indirectly labeled. In a preferred embodiment, the DBL is directly labeled, that is, the DBL comprises a label. In an alternate embodiment, the DBL is indirectly labeled; that is, a labeling binding ligand (LBL) that will bind to the DBL is used. In this embodiment, the labeling binding ligand-DBL pair can be as described above for IBL-DBL pairs.

Accordingly, the identification of the location of the individual beads (or subpopulations of beads) is done using one or more decoding steps comprising a binding between the labeled DBL and either the IBL or the capture probe (i.e. a hybridization between the candidate probe and the decoder probe when the capture probe is a nucleic acid). After decoding, the DBLs can be removed and the array can be used; however, in some circumstances, for example when the DBL binds to an IBL and not to the capture probe, the removal of the DBL is not required (although it may be desirable in some circumstances). In addition, as outlined herein, decoding may be done either before the array is used to in an assay, during the assay, or after the assay.

In one embodiment, a single decoding step is done. In this embodiment, each DBL is labeled with a unique label, such that the the number of unique tags is equal to or greater than the number of capture probes (although in some cases, "reuse" of the unique labels can be done, as described herein; similarly, minor variants of candidate probes can share the same decoder, if the variants are encoded in another dimension, i.e. in the bead size or label). For each capture probe or IBL, a DBL is made that will specifically bind to it and contains a unique tag, for example one or more fluorochromes. Thus, the identity of each DBL, both its composition (i.e. its sequence when it is a nucleic acid) and its label, is known. Then, by adding the DBLs to the array containing the capture probes under conditions which allow the formation of complexes (termed hybridization complexes when the components are nucleic acids) between the DBLs and either the capture probes or the IBLs, the location of each DBL can be elucidated. This allows the identification of the location of each capture probe; the random array has been decoded. The DBLs can then be removed, if necessary, and the target sample applied.

In a preferred embodiment, the number of unique labels is less than the number of unique capture probes, and thus a sequential series of decoding steps are used. In this embodiment, decoder probes are divided into n sets for decoding. The number of sets corresponds to the number of unique tags. Each decoder probe is labeled in n separate reactions with n distinct tags. All the decoder probes share the same n tags. The decoder probes are pooled so that each pool contains only one of the n tag versions of each decoder, and no two decoder probes have the same sequence of tags across all the pools. The number of pools required for this to be true is determined by the number of decoder probes and the n. Hybridization of each pool to the array generates a signal at every address. The sequential hybridization of each pool in turn will generate a unique, sequence-specific code for each candidate probe. This identifies the candidate probe at each address in the array. For example, if four tags are used, then 4× n sequential hybridizations can ideally distinguish $4^n$ sequences, although in some cases more steps may be required. After the hybridization of each pool, the hybrids are denatured and the decoder probes removed, so that the probes are rendered single-stranded for the next hybridization (although it is also possible to hybridize limiting amounts of target so that the available probe is not saturated. Sequential hybridizations can be carried out and analyzed by subtracting pre-existing signal from the previous hybridization).

An example is illustrative. Assuming an array of 16 probe nucleic acids (numbers 1-16), and four unique tags (four different fluors, for example; labels A-D). Decoder probes 1-16 are made that correspond to the probes on the beads. The first step is to label decoder probes 1-4 with tag A, decoder probes 5-8 with tag B, decoder probes 9-12 with tag C, and decoder probes 13-16 with tag D. The probes are mixed and the pool is contacted with the array containing the beads with the attached candidate probes. The location of each tag (and thus each decoder and candidate probe pair) is then determined. The first set of decoder probes are then removed. A second set is added, but this time, decoder probes 1, 5, 9 and 13 are labeled with tag A, decoder probes 2, 6, 10 and 14 are labeled with tag B, decoder probes 3, 7, 11 and 15 are labeled with tag C, and decoder probes 4, 8, 12 and 16 are labeled with tag D. Thus, those beads that contained tag A in both decoding steps contain candidate probe 1; tag A in the first decoding step and tag B in the second decoding step contain candidate probe 2; tag A in the first decoding step and tag C in the second step contain candidate probe 3; etc.

In one embodiment, the decoder probes are labeled in situ; that is, they need not be labeled prior to the decoding reaction. In this embodiment, the incoming decoder probe is shorter than the candidate probe, creating a 5' "overhang" on the decoding probe. The addition of labeled ddNTPs (each labeled with a unique tag) and a polymerase will allow the addition of the tags in a sequence specific manner, thus creating a sequence-specific pattern of signals. Similarly, other modifications can be done, including ligation, etc.

In addition, since the size of the array will be set by the number of unique decoding binding ligands, it is possible to "reuse" a set of unique DBLs to allow for a greater number of test sites. This may be done in several ways; for example, by using some subpopulations that comprise optical signatures. Similarly, the use of a positional coding scheme within an array; different sub-bundles may reuse the set of DBLs. Similarly, one embodiment utilizes bead size as a coding modality, thus allowing the reuse of the set of unique DBLs for each bead size. Alternatively, sequential partial loading of arrays with beads can also allow the reuse of DBLs. Furthermore, "code sharing" can occur as well.

In a preferred embodiment, the DBLs may be reused by having some subpopulations of beads comprise optical signatures. In a preferred embodiment, the optical signature is generally a mixture of reporter dyes, preferably fluorescent. By varying both the composition of the mixture (i.e. the ratio of one dye to another) and the concentration of the dye (leading to differences in signal intensity), matrices of unique optical signatures may be generated. This may be done by covalently attaching the dyes to the surface of the beads, or alternatively, by entrapping the dye within the bead.

In a preferred embodiment, the encoding can be accomplished in a ratio of at least two dyes, although more encoding dimensions may be added in the size of the beads, for example. In addition, the labels are distinguishable from one another; thus two different labels may comprise different molecules (i.e. two different fluors) or, alternatively, one label at two different concentrations or intensity.

In a preferred embodiment, the dyes are covalently attached to the surface of the beads. This may be done as is generally outlined for the attachment of the capture probes, using functional groups on the surface of the beads. As will be appreciated by those in the art, these attachments are done to minimize the effect on the dye.

In a preferred embodiment, the dyes are non-covalently associated with the beads, generally by entrapping the dyes in the pores of the beads.

Additionally, encoding in the ratios of the two or more dyes, rather than single dye concentrations, is preferred since it provides insensitivity to the intensity of light used to interrogate the reporter dye's signature and detector sensitivity.

In a preferred embodiment, a spatial or positional coding system is done. In this embodiment, there are sub-bundles or subarrays (i.e. portions of the total array) that are utilized. By analogy with the telephone system, each subarray is an "area code", that can have the same tags (i.e. telephone numbers) of other subarrays, that are separated by virtue of the location of the subarray. Thus, for example, the same unique tags can be reused from bundle to bundle. Thus, the use of 50 unique tags in combination with 100 different subarrays can form an array of 5000 different capture probes. In this embodiment, it becomes important to be able to identify one bundle from another; in general, this is done either manually or through the use of marker beads, i.e. beads containing unique tags for each subarray.

In alternative embodiments, additional encoding parameters can be added, such as microsphere size. For example, the use of different size beads may also allow the reuse of sets of DBLs; that is, it is possible to use microspheres of different sizes to expand the encoding dimensions of the microspheres. Optical fiber arrays can be fabricated containing pixels with different fiber diameters or cross-sections; alternatively, two or more fiber optic bundles, each with different cross-sections of the individual fibers, can be added together to form a larger bundle; or, fiber optic bundles with fiber of the same size cross-sections can be used, but just with different sized beads. With different diameters, the largest wells can be filled with the largest microspheres and then moving onto progressively smaller microspheres in the smaller wells until all size wells are then filled. In this manner, the same dye ratio could be used to encode microspheres of different sizes thereby expanding the number of different oligonucleotide sequences or chemical functionalities present in the array. Although outlined for fiber optic substrates, this as well as the other methods outlined herein can be used with other substrates and with other attachment modalities as well.

In a preferred embodiment, the coding and decoding is accomplished by sequential loading of the microspheres into the array. As outlined above for spatial coding, in this embodiment, the optical signatures can be "reused". In this embodiment, the library of microspheres each comprising a different capture probe (or the subpopulations each comprise a different capture probe), is divided into a plurality of sublibraries; for example, depending on the size of the desired array and the number of unique tags, 10 sublibraries each comprising roughly 10% of the total library may be made, with each sublibrary comprising roughly the same unique tags. Then, the first sublibrary is added to the fiber optic bundle comprising the wells, and the location of each capture probe is determined, generally through the use of DBLs. The second sublibrary is then added, and the location of each capture probe is again determined. The signal in this case will comprise the signal from the "first" DBL and the "second" DBL; by comparing the two matrices the location of each bead in each sublibrary can be determined. Similarly, adding the third, fourth, etc. sublibraries sequentially will allow the array to be filled.

In a preferred embodiment, codes can be "shared" in several ways. In a first embodiment, a single code (i.e. IBL/DBL pair) can be assigned to two or more agents if the target sequences different sufficiently in their binding strengths. For example, two nucleic acid probes used in an mRNA quantitation assay can share the same code if the ranges of their hybridization signal intensities do not overlap. This can occur, for example, when one of the target sequences is always present at a much higher concentration than the other. Alternatively, the two target sequences might always be present at a similar concentration, but differ in hybridization efficiency.

Alternatively, a single code can be assigned to multiple agents if the agents are functionally equivalent. For example, if a set of oligonucleotide probes are designed with the common purpose of detecting the presence of a particular gene, then the probes are functionally equivalent, even though they may differ in sequence. Similarly, an array of this type could be used to detect homologs of known genes. In this embodiment, each gene is represented by a heterologous set of probes, hybridizing to different regions of the gene (and therefore differing in sequence). The set of probes share a common code. If a homolog is present, it might hybridize to some but not all of the probes. The level of homology might be indicated by the fraction of probes hybridizing, as well as the average hybridization intensity. Similarly, multiple antibodies to the same protein could all share the same code.

In a preferred embodiment, decoding of self-assembled random arrays is done on the bases of pH titration. In this embodiment, in addition to capture probes, the beads comprise optical signatures, wherein the optical signatures are generated by the use of pH-responsive dyes (sometimes referred to herein as "ph dyes") such as fluorophores. This embodiment is similar to that outlined in PCT US98/05025 and U.S. Ser. No. 09/151,877, both of which are expressly incorporated by reference, except that the dyes used in the present ivention exhibits changes in fluorescence intensity (or other properties) when the solution pH is adjusted from below the pKa to above the pKa (or vice versa). In a preferred embodiment, a set of pH dyes are used, each with a different pKa, preferably separated by at least 0.5 pH units. Preferred embodiments utilize a pH dye set of pka's of 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11, and 11.5. Each bead can contain any subset of the pH dyes, and in this way a unique code for the capture probe is generated. Thus, the decoding of an array is achieved by titrating the array from pH 1 to pH 13, and measuring the fluorescence signal from each bead as a function of solution pH.

Thus, the present invention provides array compositions comprising a substrate with a surface comprising discrete sites. A population of microspheres is distributed on the sites, and the population comprises at least a first and a second subpopulation. Each subpopulation comprises a capture probe, and, in addition, at least one optical dye with a given pKa. The pkas of the different optical dyes are different.

In a preferred embodiment, several levels of redundancy are built into the arrays of the invention. Building redundancy into an array gives several significant advantages, including the ability to make quantitative estimates of confidence about the data and signficant increases in sensitivity. Thus, preferred embodiments utilize array redundancy. As will be appreciated by those in the art, there are at least two types of redundancy that can be built into an array: the use of multiple identical sensor elements (termed herein "sensor redundancy"), and the use of multiple sensor elements directed to the same target analyte, but comprising different chemical functionalities (termed herein "target redundancy"). For example, for the detection of nucleic acids, sensor redundancy utilizes of a plurality of sensor elements such as beads comprising identical binding ligands such as probes. Target redundancy utilizes sensor elements with different probes to the same target: one probe may span the first 25 bases of the target, a second probe may span the second 25 bases of the target, etc. By building in either or both of these types of redundancy into an array, significant benefits are obtained. For example, a variety of statistical mathematical analyses may be done.

In addition, while this is generally described herein for bead arrays, as will be appreciated by those in the art, this techniques can be used for any type of arrays designed to detect target analytes.

In a preferred embodiment, sensor redundancy is used. In this embodiment, a plurality of sensor elements, e.g. beads, comprising identical bioactive agents are used. That is, each subpopulation comprises a plurality of beads comprising identical bioactive agents (e.g. binding ligands). By using a number of identical sensor elements for a given array, the optical signal from each sensor element can be combined and any number of statistical analyses run, as outlined below. This can be done for a variety of reasons. For example, in time varying measurements, redundancy can significantly reduce the noise in the system. For non-time based measurements, redundancy can significantly increase the confidence of the data.

In a preferred embodiment, a plurality of identical sensor elements are used. As will be appreciated by those in the art, the number of identical sensor elements will vary with the application and use of the sensor array. In general, anywhere from 2 to thousands may be used, with from 2 to 100 being preferred, 2 to 50 being particularly preferred and from 5 to 20 being especially preferred. In general, preliminary results indicate that roughly 10 beads gives a sufficient advantage, although for some applications, more identical sensor elements can be used.

Once obtained, the optical response signals from a plurality of sensor beads within each bead subpopulation can be manipulated and analyzed in a wide variety of ways, including baseline adjustment, averaging, standard deviation analysis, distribution and cluster analysis, confidence interval analysis, mean testing, etc.

In a preferred embodiment, the first manipulation of the optical response signals is an optional baseline adjustment. In a typical procedure, the standardized optical responses are adjusted to start at a value of 0.0 by subtracting the integer 1.0 from all data points. Doing this allows the baseline-loop data to remain at zero even when summed together and the random response signal noise is canceled out. When the sample is a fluid, the fluid pulse-loop temporal region, however, frequently exhibits a characteristic change in response, either positive, negative or neutral, prior to the sample pulse and often requires a baseline adjustment to overcome noise associated with drift in the first few data points due to charge buildup in the CCD camera. If no drift is present, typically the baseline from the first data point for each bead sensor is subtracted from all the response data for the same bead. If drift is observed, the average baseline from the first ten data points for each bead sensor is substracted from the all the response data for the same bead. By applying this baseline adjustment, when multiple bead responses are added together they can be amplified while the baseline remains at zero. Since all beads respond at the same time to the sample (e.g. the sample pulse), they all see the pulse at the exact same time and there is no registering or adjusting needed for overlaying their responses. In addition, other types of baseline adjustment may be done, depending on the requirements and output of the system used.

Once the baseline has been adjusted, a number of possible statistical analyses may be run to generate known statistical parameters. Analyses based on redundancy are known and generally described in texts such as Freund and Walpole, Mathematical Statistics, Prentice Hall, Inc. New Jersey, 1980, hereby incorporated by reference in its entirety.

In a preferred embodiment, signal summing is done by simply adding the intensity values of all responses at each time point, generating a new temporal response comprised of the sum of all bead responses. These values can be baseline-adjusted or raw. As for all the analyses described herein, signal summing can be performed in real time or during post-data acquisition data reduction and analysis. In one embodiment, signal summing is performed with a commercial spreadsheet program (Excel, Microsoft, Redmond, Wash.) after optical response data is collected.

In a preferred embodiment, cummulative response data is generated by simply adding all data points in successive time intervals. This final column, comprised of the sum of all data points at a particular time interval, may then be compared or plotted with the individual bead responses to determine the extent of signal enhancement or improved signal-to-noise ratios.

In a preferred embodiment, the mean of the subpopulation (i.e. the plurality of identical beads) is determined, using the well known Equation 1:

$$\mu = \sum \frac{x_i}{n} \qquad \text{Equation 1}$$

In some embodiments, the subpopulation may be redefined to exclude some beads if necessary (for example for obvious outliers, as discussed below).

In a preferred embodiment, the standard deviation of the subpopulation can be determined, generally using Equation 2 (for the entire subpopulation) and Equation 3 (for less than the entire subpopulation):

$$\sigma = \sqrt{\frac{\sum (x_i - \mu)^2}{n}} \qquad \text{Equation 2}$$

$$s = \sqrt{\frac{\sum (x_i - \bar{x})^2}{n - 1}} \qquad \text{Equation 3}$$

As for the mean, the subpopulation may be redefined to exclude some beads if necessary (for example for obvious outliers, as discussed below).

In a preferred embodiment, statistical analyses are done to evaluate whether a particular data point has statistical validity within a subpopulation by using techniques including, but not limited to, t distribution and cluster analysis. This may be done to statistically discard outliers that may otherwise skew the result and increase the signal-to-noise ratio of any particular experiment. This may be done using Equation 4:

$$t = \frac{\bar{x} - \mu}{s/\sqrt{n}} \qquad \text{Equation 4}$$

In a preferred embodiment, the quality of the data is evaluated using confidence intervals, as is known in the art. Confidence intervals can be used to facilitate more comprehensive data processing to measure the statistical validity of a result.

In a preferred embodiment, statistical parameters of a subpopulation of beads are used to do hypothesis testing. One application is tests concerning means, also called mean testing. In this application, statistical evaluation is done to determine whether two subpopulations are different. For example, one sample could be compared with another sample for each subpopulation within an array to determine if the variation is statistically significant.

In addition, mean testing can also be used to differentiate two different assays that share the same code. If the two assays give results that are statistically distinct from each other, then the subpopulations that share a common code can be distinguished from each other on the basis of the assay and the mean test, shown below in Equation 5:

$$z = \frac{\bar{x}_1 - \bar{x}_2}{\sqrt{\frac{\sigma_1^2}{n_1} + \frac{\sigma_2^2}{n_2}}} \qquad \text{Equation 5}$$

Furthermore, analyzing the distribution of individual members of a subpopulation of sensor elements may be done. For example, a subpopulation distribution can be evaluated to determine whether the distribution is binomial, Poisson, hypergeometric, etc.

In addition to the sensor redundancy, a preferred embodiment utilizes a plurality of sensor elements that are directed to a single target analyte but yet are not identical. For example, a single target nucleic acid analyte may have two or more sensor elements each comprising a different probe. This adds a level of confidence as non-specific binding interactions can be statistically minimized. When nucleic acid target analytes are to be evaluated, the redundant nucleic acid probes may be overlapping, adjacent, or spatially separated. However, it is preferred that two probes do not compete for a single binding site, so adjacent or separated probes are preferred. Similarly, when proteinaceous target analytes are to be evaluated, preferred embodiments utilize bioactive agent binding agents that bind to different parts of the target. For example, when antibodies (or antibody fragments) are used as bioactive agents for the binding of target proteins, preferred embodiments utilize antibodies to different epitopes.

In this embodiment, a plurality of different sensor elements may be used, with from about 2 to about 20 being preferred, and from about 2 to about 10 being especially preferred, and from 2 to about 5 being particularly preferred, including 2, 3, 4 or 5. However, as above, more may also be used, depending on the application.

As will be appreciated by those in the art, the present invention finds use in a wide variety of applications.

In a preferred embodiment, the present invention finds use in gene expression monitoring and profiling in any mRNA sample, and in particular in the comparison of different cellular states, including the comparison of diseased tissue such as cancerous tissue with normal tissue.

In a preferred embodiment, the present invention finds use in alternative splice analysis, including both discovery of splice junctions and detection of alternative splice junctions. In this embodiment, the invention finds use in the correlation of alternative splicing patterns to morphological and clinical parameters of cancer. Similarly, the mechanisms and regulation of constitutive and alternative splicing can be elucidated in a variety of cell types, as outlined above.

Specific splicing targets are shown below in Table 1 (followed by the references).

TABLE I

Selected Splicing targets

| | Gene Name | Functional Significance | Selected Reference |
|---|---|---|---|
| 1 | acetylcholinesteras | synapse maturation | 1 |
| 2 | agrin | AChR clustering at synapses | 2 |
| 3 | AML1 | transcriptional activation | 3 |
| 4 | ASF/SF2 | mRNA splicing regulation | 4 |
| 5 | Bcl-x | apoptosis regulation | 5 |
| 6 | BRCA1 | transcriptional activation | 6 |
| 7 | c-src | signal transduction regulation | 7 |
| 8 | calcium channel, alpha 1A | neurotransmitterrelease | 8 |
| 9 | calcium channel, alpha 1B | neurotransmitterrelease | 9 |
| 10 | caspase 1 (ICE) | apoptotic regulation | 10 |
| 11 | caspase 2 (Ich-1) | apoptotic regulation | 11 |
| 12 | CD45 | T cell maturation | 12 |
| 13 | clathrin light chain B | receptor-mediatedendocytosis | 13 |
| 14 | cytochrome P450, aromatase | steroid hormone synthesis | 14 |
| 15 | estrogen receptor 1 | hormone response | 15 |
| 16 | estrogen receptor 2 | hormone response | 16 |
| 17 | fas ligand | apoptotic regulation | 17 |
| 18 | FGFR2 | signal transduction | 18 |
| 19 | fibronectin 1 | wound healing | 19 |
| 20 | fyn | growth control | 20 |
| 21 | glutamate receptor NMDAR1 | neurotransmission | 21 |
| 22 | Hel-N1 | mRNA turnover | 22 |
| 23 | insulin receptor | signal transduction | 23 |
| 24 | integrin beta | cell adhesion | 24 |
| 25 | jun kinase 2 | transcriptionalcofactor | 25 |
| 26 | MUC1 | cell surface tumor marker | 26 |
| 27 | myosin heavy chain | muscle contraction | 27 |
| 28 | NCAM | cell adhesion | 28 |
| 29 | nNos | neurotransmission | 29 |
| 30 | p15 CDK inhibitor 2B (INK 4b) | cell cycle control | 30 |
| 31 | p16 CDK inhibitor 2A-(ARF) | cell cycle control | 31 |
| 32 | presenilin 2 | apoptotic regulation | 32 |
| 33 | prostate-specificantigen | cell surface tumor marker | 33 |
| 34 | SMN | spinal motor neuron survival | 34 |
| 35 | SRp40 | mRNA splicing regulation | 35 |
| 36 | tau | neuronal maturation | 36 |
| 37 | telomerase | chromosomal integrity and growth control | 37 |
| 38 | transformer 2 beta | mRNA splicing regulation | 38 |
| 39 | tropomyosin 1 (alpha) | muscle contraction | 39 |
| 40 | tropomyosin 2 (beta) | muscle contraction | 40 |
| 41 | troponin 13 | muscle contraction | 41 |
| 42 | VEGFR-1 | angiogenesis and vascular permeability | 42 |
| 43 | Wilms tumor 1 | transciptional regulation | 43 |

As above, any number of statistical analyses may be run on the data from target redundant sensors.

One benefit of the sensor element summing (referred to herein as "bead summing" when beads are used), is the increase in sensitivity that can occur.

SELECTED REFERENCE FOR TABLE I

1. Luo, Z. D., et al., *J. Biol. Chem.* 273:28486-28495 (1998).
2. Ferns, M., et al., *Neuron,* 8:1079-1086 (1992).
3. Tanaka, T., et al., *Leukemia* 11 Suppl 3:299-302 (1997).

4. Ge, H., et al., *Cell* 66:373-382 (1991).
5. Boise, L. H., et al., *Cell* 74:597-608 (1993).
6. Cui, J. Q., et al., *Oncol. Rep.* 5:585-589 (1998).
7. Modafferi, E. F., et al., *RNA* 5:687-706 (1999).
8. Bourinet, E., et al., *Nat. Neurosci.* 2:407-415 (1999).
9. Lin, Z., et al., *J. Neurosci.* 19:5322-5331 (1999).
10. Alnemri, E. S., et al., *J. Biol. Chem.* 270:4312-4317 (1995).
11. Jiang, Z. H., et al., *Proc. Natl. Acad. Sci.* 95:9155-9160 (1998).
12. Ratech, H., et al., *Cell. Immunol.* 177:109-118 (1997).
13. Daoud, R., et al., *Eur. J. Neurosci.* 11:788-802 (1999).
14. Utsumi, T., et al., *J. Clin. Endo. Metab.* 81:2344-2349 (1996).
15. Balleine, R. L., et al., *J. Clin. Endo. Metab.* 84:1370-1377 (1999).
16. Hanstein, B., et al., *Mol. Endo.* 13:129-137 (1999).
17. Ruberti, G., et al., *Adv. Exper. Med. Biol.* 406:125-134 (1996).
18. Luqmani, Y. A., et al., *Intl. J. Cancer* 64:274-279 (1995).
19. Vogelezang, M. G., et al., *J. Neurosci. Res.* 56:323-333 (1999).
20. Weil, R., et al., *J. Virol.* 73:3709-3717 (1999).
21. Koltchine, V. V., et al., *Brain Res. Mol. Brain Res.* 39:99-108 (1996).
22. King, P. H., *Gene* 151:261-265 (1994).
23. Moller, D. E., et al., *Mol. Endo.* 3:1263-1269 (1989).
24. Meredith, J., Jr., et al., *Science* 269:1570-1572 (1995).
25. Bost, F., et al., *Mol. Cell. Biol.* 19:1938-1949 (1999).
26. Baruch, A., et al., *Cancer Res.* 59:1552-1561 (1999).
27. Haase, H., et al., *J. Cell. Biochem.* 60:521-528 (1996).
28. Rafuse, V. F., et al., *J. Cell Biol.* 132:969-983 (1996).
29. Wang, Y., et al., *Crit. Rev. Neurobiol.* 13:21-43 (1999).
30. Tsubari, M., et al., *Cancer Res.* 57:2966-2973 (1997).
31. Robertson, K. D., et al., *Oncogene* 18:3810-3820 (1999).
32. Sato, N., et al., *J. Neurochem.* 72:2498-505 (1999).
33. Su, S. L., et al., *Cancer Res.* 55:1441-1443 (1995).
34. Lorson, C. L., et al., *Proc. Natl. Acad. Sci.* 96:6307-6311 (1999).
35. Du, K., et al., *J. Biol. Chem.* 273:35208-35215 (1998).
36. Varani, L., et al., *Proc. Natl. Acad. Sci.* 96:8229-8234 (1999).
37. Ulaner, G. A., et al., *Cancer Res.* 58:4168-72 (1998).
38. Daoud, R., et al., *Eur. J. Neurosci.* 11:788-802 (1999).
39. Kashiwada, K., et al., *J. Biol. Chem.* 272:15396-15404 (1997).
40. Gimona, M., et al., *Proc. Natl. Acad. Sci.* 92:9776-9780 (1995).
41. Ogut, O., et al., *Am. J. Physiol.* 276:C 1162-1170 (1999).
42. He, Y., et al., *Mol. Endo.* 13:537-545 (1999).
43. Webster, N. J., et al., *Biochem. Mo. Med.* 62:139-150 (1997).

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

All references cited herein are incorporated by reference in their entirety, particularly PCT applications WO 00/60332; WO 99/45357; WO 00/16101; WO 99/67641; PCT/US00/13942; WO 00/48000; WO 00/47996; WO 00/63437.

EXAMPLE 1

Experimental Strategy

In order to detect mRNA isoforms as well as closely related transcripts for profiling both gene expression and alternative splicing, an assay was developed using an addressable approach (FIG. 12a). Using a 5' alternative splicing scenario as an example, two DNA oligonucleotides were designed for the two competing 5' splice sites and one for the common 3' splice site (FIG. 12b). The 5' splice site oligonucleotides are also linked to unique "address" sequences. These addresses allow sorting of individual splicing events on a universal address array. Both 5' and 3' oligonucleotides are also flanked by common PCR primer binding sites (T3 at one end and T7 at the other). The assay consists of five steps (FIG. 12c): (1) RNA annealing: A mix of specific oligonucleotides and biotinylated oligo-dT are hybridized to total RNA. (2) Poly (A+) selection: Polyadenylated mRNAs are selected through binding of biotinylated oligo-dT to streptavidin coated on tube wells. mRNAs along with annealed oligonucleotides are therefore transferred from solution to the solid phase. This permits removal of free oligonucleotides (which can be nonspecifically ligated in solution). Furthermore, washing and buffer changes can be carried out without ethanol precipitation and centrifugation. In fact, cells can be directly lysed in the presence of oligonucleotides followed by poly (A+) selection, thereby omitting RNA extraction and purification for the assay. (3) RNA-mediated oligonucleotide ligation: As a result of splicing, specific upstream and downstream oligonucleotides are paired and ligated by T4 DNA ligase. This ligation step ensures the specificity and stringency of the assay such that only juxtaposed oligonucleotides will be ligated, forming a complete amplicon for PCR. (4) Signal amplification by PCR: Biotinylated T7 and unmodified T3 primers are used to amplify the ligation products, resulting in increased sensitivity. In addition, the uniform length of amplicons minimizes bias introduced during PCR. (5) Chip hybridization: Individual splicing events are detected and quantified by hybridization on an address array. This assay is known as the RNA Annealing, Selection, Ligation assay (RASL).

Specificity and Sensitivity of the RASL Assay

Adenovirus E1A system was used to validate the experimental design and determine conditions for the RASL procedure. E1A pre-mRNA gives rise to three mRNA isoforms 9S, 12S, and 13S by using three alternative 5' splice sites, which compete for a common 3' splice site (FIG. 13a). In COS cells co-transfected with the alternative splicing factor ASF, splice site selection is shifted to the proximal 13S splice site as previously reported. No signal was detected by RT-PCR in mock-transfected cells and all three isoforms were detected in cells transfected with E1A. When co-transfected with ASF, 9S was reduced, 12S was almost eliminated, and 13S became the predominant isoform. One microgram total RNA from each sample was then subject to RASL. Again, no signal was detected in mock-transfected cells and the RASL products were seen in both E1A and E1A plus ASF-transfected cells (data not shown. Because these PCR products were of identical lengths, each band represents a mixture of E1A isoforms. The PCR products were analyzed on the address arrays. No signal was detected in mock-transfected cells; specific signals for 9S, 12S, and 13S were detected in E1A-transfected cells; and the signal for 13S was by far the strongest in E1A plus ASF-transfected cells. Comparison between the results from the RT-PCR and RASL analyses clearly demonstrate that both methods give rise to comparable quantitative differences of E1A splicing induced by ASF (FIG. 13b).

Because the E1A reporter in transfected COS cells was likely overexpressed, it was determined whether RASL could be used to detect endogenous mRNA isoforms. Taking advantage of the fact that 293T cells carry an integrated type 5 Adenovirus, RASL was applied to RNA from 293T cells as well as to control RNA from HeLa cells. RT-PCR analysis revealed a comparable level of expression of 12S and 13S, but little 9S isoform in 293T cells (data not shown). As predicted, a strong signal was also detected by RASL in 239T, but not in HeLa cells, indicating that the assay is highly specific in detecting endogenously expressed messages.

Figure 14:
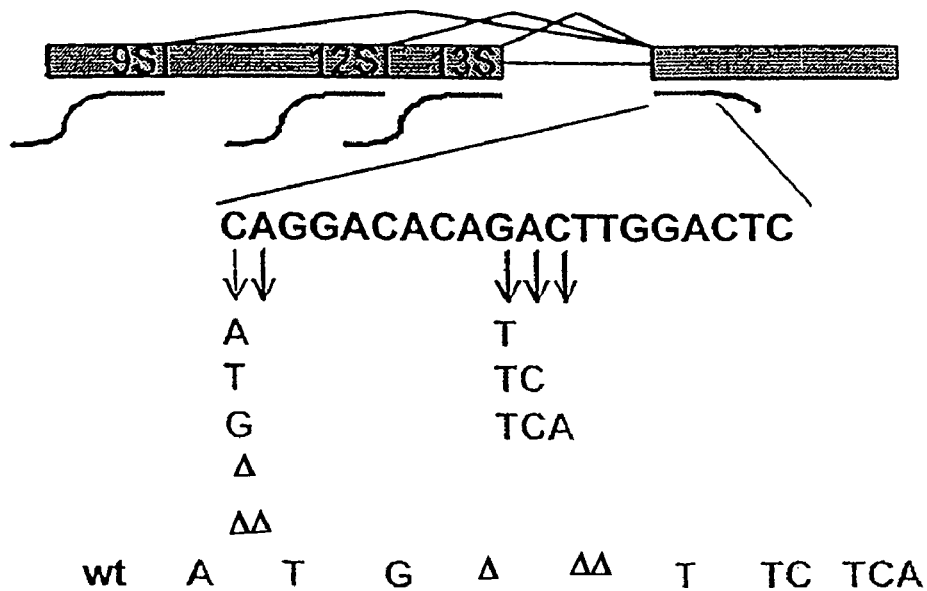
FIG. 14 (SEQ ID NOS:1-9) Specificity of RASL. Point mutations and base deletions were individually introduced into the common oligonucleotide as illustrated and each was tested in the presence of all three wild type upstream oligonucleotides. The RASL products were analyzed in an agarose gel (not shown) as well as on the address assays.

To document the specificity of the RASL assay, a series of mutations were introduced into the E1A common oligonucleotide and tested individually in combination with wild type upstream oligonucleotides (FIG. 14; SEQ ID NOS:1-9). Point mutations at the terminus reduced the signal to background with the exception of T substitution for C in the case of 12S, likely due to wobble basepairing between T and G in the opposite strand. Deletion of one or two bases at the terminus abolished the signal. Mismatch mutations in the middle also were tested. This allowed for titration of the annealing temperature such that a single base mismatch in the middle was allowed to produce some signal.

Finally, the sensitivity of the RASL assay was examined using the E1A model. Taking advantage of the fact that E1A is expressed in 293T cells, but not in HeLa cells, a serial dilution of 293T RNA into a fixed amount (1 ug) of total HeLa RNA was prepared and then subjected to RASL (FIG. 15a). The 12S E1A signal could be clearly detected with 10 pg of 293T RNA, which corresponds to about 1 cell. To determine the ability to detect expression from single cells, limited dilution of 293T cells in 96-well microtiter plates were prepared followed by counting the actual cell number in each well under a microscope. Cells were then directly lysed in the annealing buffer containing 0.1% SDS and tRNA carrier, and mRNA was captured in streptavidin-coated tubes for RASL analysis (FIG. 15b). The data clearly showed detection of E1A isoforms from a single cell.

EXAMPLE 2

Multiplex Analysis of mRNA Isoforms

Figure 16:
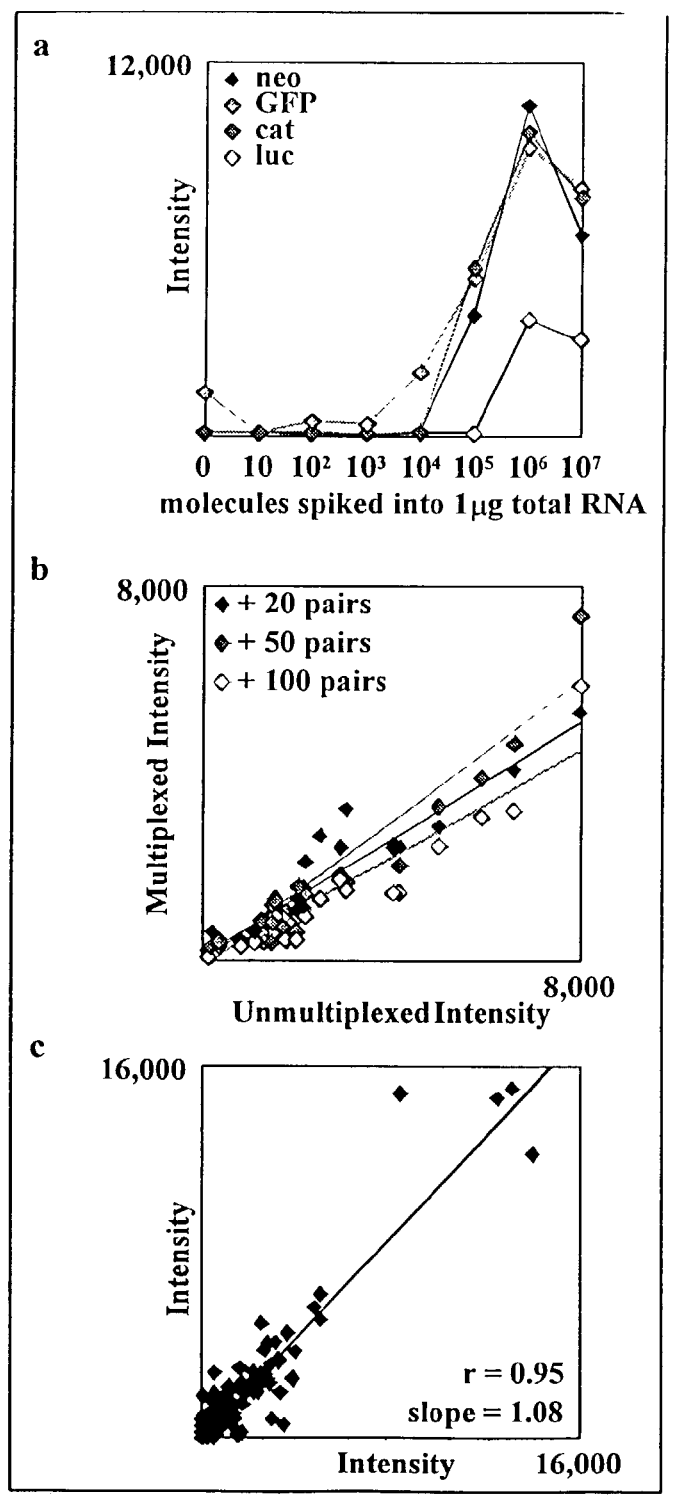
FIG. 16 Multiplex analysis by RASL. a. The detection range on fiber optic arrays using spiked RNAs. Poly(A)-tailed nonhuman RNAs were transcribed in vitro and spiked into total HeLa RNA. The results show about 100-fold detection range with RASL. b. 10 mRNA isoforms were analyzed in the presence of an increasing number of other targets. The result indicates that the impact of multiplexing at the current level is minimal. c. Reproducibility of multiplexed RASL. The expression of 100 mRNA isoforms in five cell lines was assayed in duplicate and the results are plotted with one set of data against the duplicate.

To determine the detection range in in multi-plexed reactions, four poly(A)-tailed nonhuman RNAs were prepared and spiked into 1 ug of total HeLa RNA (FIG. 16a). Three of them were detectable from 104 to 106 molecules, but the detection sensitivity was much lower with the luc RNA.

To address multiplexing and reproducibility, 100 transcripts were selected for profiling gene expression and 100 isoforms from 23 genes for analysis of alternative splicing. 10 mRNA isoforms were quantified in the presence of an increasing number of other targets to determine the potential interference in the multiplex situation (FIG. 16b). The data indicate that the impact of multiplexing at the current complexity appears rather minimal as the signals from the 10 reference targets remained unaltered when assayed in the presence of up to 100 other targets.

To demonstrate the reproducibility of the assay, the expression of 100 isoforms in 5 cell lines were assayed in duplicate and plotted one set of data against the duplicate (FIG. 16c). The data clearly illustrate the reproducibility of the assay as indicated by the r value of 0.95.

EXAMPLE 3

Profiling Gene Expression and Alternative Splicing in Cancer Cells

Figure 17:
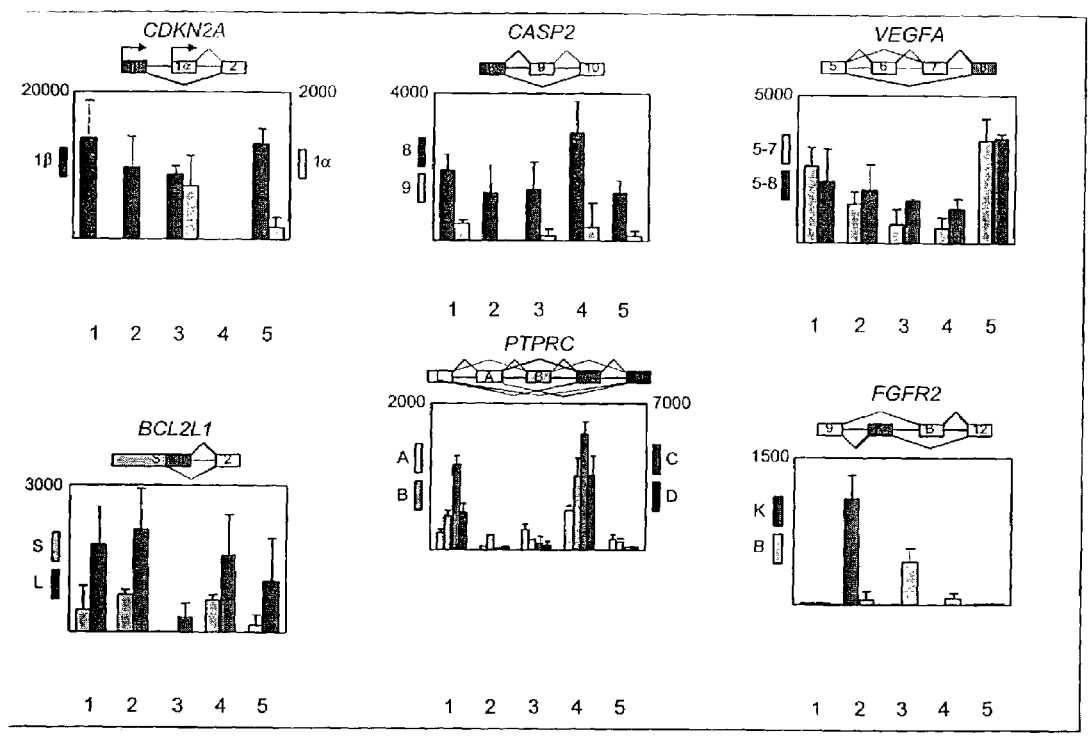
FIG. 17 Isoform expression of six genes in five human cancer cell lines determined by both multiplexed RASL and RT-PCR. In each panel, the gene name and reported pattern of alternative splicing are labeled on top. For analysis by RASL, individual alternative exons were linked to unique address sequences. Triplicate RASL data are presented in bars and the linear scales are labeled on the left. In the cases where different scales are used for different isoforms (at discussed earlier, different target oligos and address sequences have distinct kinetic properties, and thus, it is only meaningful to compare the same target in different samples, rather than between targets), the scale and the isoform are coordinately labeled on a given side. In the cases of CDKN2A (p16/p14ARF) and FGFR2 (FGFR2/KGFR), two sets of primers were needed to amplify their isoforms. Cell lines analyzed are: 1, U-937 (histiocytic lymphoma); 2, HT-29 (colorectal adenocarcinoma); 3, 293T (Ad5 transformed embryonic kidney); 4, Jurkat (acute T cell leukemia); 5, HeLa (cervical adenocarcinoma).

The expression of the selected targets in a number of human cancer cell lines were examined. Using the "array of arrays" format, multiplexed RASL was conducted in triplicate with RNA samples from five cell lines and six specific genes were chosen to determine their isoform expression by RT-PCR (FIG. 17).

The p16/14ARF gene (CDKN2A) plays a critical role in cell cycle control. This gene encodes two proteins using two promoters (1a for p16 and 1b for p14ARF). Remarkably, the a and b exons transcribed from their promoters are spliced to the second common exon, but linked to two different reading frames in the second exon to encode the protein products. As a result, p16 and p14ARF share no sequence homology at the protein level. p16 is known to control cell cycle through the Rb pathway whereas p14ARF is involved in the p53 pathway. Both RASL and RT-PCR yielded similar expression profiles of the two isoforms in cell lines 1, 3, 4, and 5. In cell line 2, the level of p14ARF was high as detected by RT-PCR, but this high level of expression was not reflected in the RASL assay, which may be due to the quenching effect on the array as discussed earlier with spiked RNAs.

Interestingly, the data show remarkably distinct patterns of isoform expression in different cancer cell types, indicating that the cells examined here may employ distinct mechanisms to regulate their cell cycle. The dramatic difference in isoform expression of this gene among different cancer cells suggests that the expression pattern of the gene may be a good candidate for molecular classification of cancer in future studies.

It has been reported that many apoptosis regulator genes express mRNA isoforms, which often encode proteins with opposite functions in the regulation of cell death. The CASP2 gene expresses two isoforms through inclusion or exclusion of exon 9. The exon 9-included form encodes an anti-apoptotic form of the protein whereas the exon 9-excluded form encodes a protein with a positive role in apoptosis. The five cell lines surveyed appear to express predominantly the apoptotic form as determined by RT-PCR. Very similar data were also obtained by RASL although some quantitative differences were evident between the two assays. Similar to CASP2, another apoptosis regulator Bcl-x (BCL2L1) also expresses two isoforms by using two 5' splice sites. The L form is pro-apoptotic and the S form is anti-apoptotic. Differences in isoform expression appear to be more variable among different cell lines and very similar quantitative results were obtained by both RT-PCR and RASL. The VEGF-A gene expresses multiple isoforms with distinct angiogenesis potentials. The two isoforms are widely expressed in all cell lines examined. Again, both RT-PCR and RASL gave similar results with some quantitative discrepancies.

Examination of the CD45 (PTPRC) gene expression reveals a limitation of the RASL assay. This receptor tyrosine phosphatase is known to play a critical role in T cell signaling. The gene is exclusively expressed in cells of hemopoietic lineage, which is consistent with its expression in both U-937 and Jurkat cells detected by both RT-PCR and RASL. Different isoforms can be easily distinguished by RT-PCR because of size differences. In contrast, the isoform variations were not evident by RASL (note that oligonucleotides were included in the assay for all potential combinations of alternative exons). The problem may be overcome in future experiments by using distinct sets of addressed (for alternative exons) and unaddressed (for common exons) oligonucleotides in different pools.

Revealing a Potential Autocrine Mechanism in Colorectal Adenocarcinoma and Choriocarcinoma By far, the most striking difference is the expression of the FRGR/KGFR (the gene is known as FGFR2) isoforms among different cancer cell lines and both RT-PCR and RASL revealed identical results (FIG. 17, the right panel at the bottom, and FIG. 18a). It has been reported that the FGFR2 gene expresses the isoforms using two mutually exclusive exons. The B form is expressed in fibroblasts and other cell types whereas the K form is exclusively expressed in epithelial cells.

Figure 18:
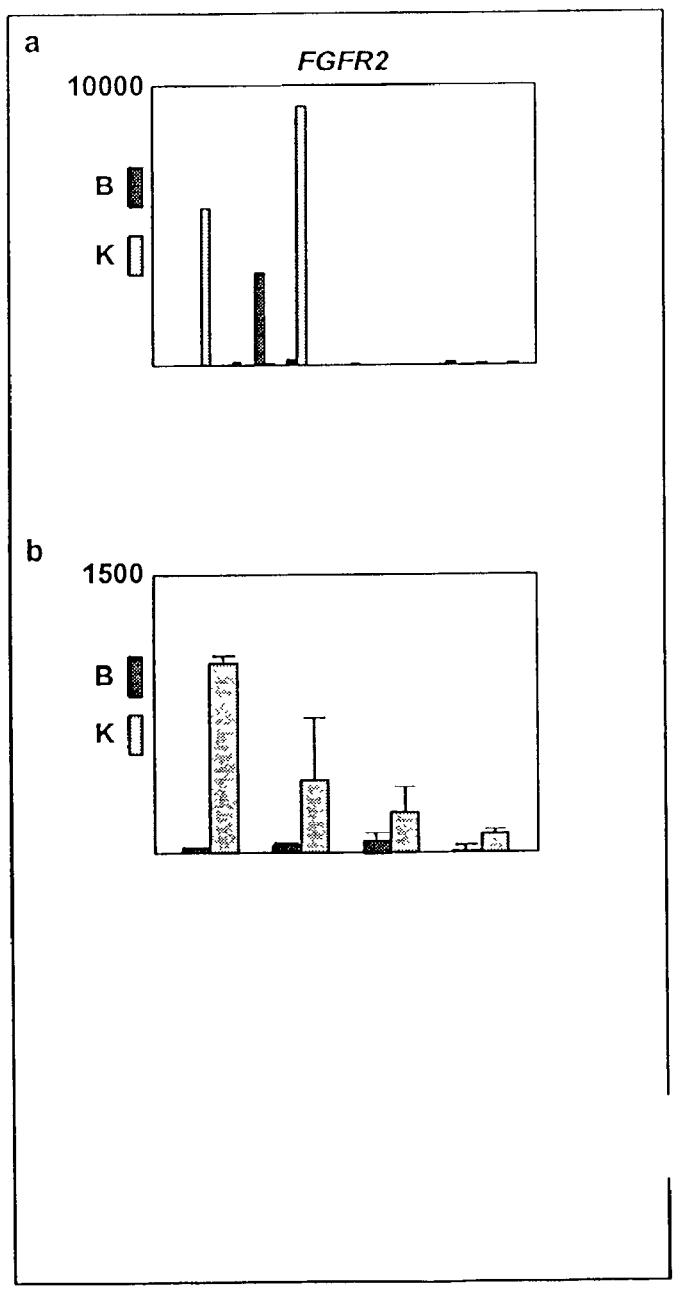
FIG. 18 FGFR/KGFR expression in human cancer cells. a. The expression of the FGFR and KGFR isoforms was examined in a panel of human cancer cell lines. The array data were derived from a standard multiplexed RASL assay (in which 1/10 of RASL products was subject to signal amplification by PCR). The same RNA samples were analyzed by RT-PCR for 28 cycles (not shown). b. Analysis of all existing human prostate cancer cell lines by "sensitized" RASL (in which all RASL products were used for PCR amplification).

Normally, fibroblasts secrets keratinocyte growth factor (KGF) whereas epithelial cells secrets fibroblast growth factor (FGF), thereby forming a paracrine loop for growth control in development. It has also been suggested that certain epithelial prostate cancer cells express both FGF and FGFR (due to a switch from the K to B form), therefore creating an autocrine loop, which may contribute to uncontrolled growth of prostate tumor cells. To test this hypothesis, a large panel of human cancer cell lines were examined by both RT-PCR and RASL (FIG. 18).

Surprisingly, human prostate cancer cell lines do not express a detectable level of FGFR/KGFR expression under standard assay conditions by either RASL or RT-PCR (FIG. 18a). This was further investigated by pushing RASL and RT-PCR to maximal sensitivity (FIG. 18b). Indeed, as previously reported, androgen-sensitive LNCaP cells expresse the K form whereas some switch from K to B was detected in androgen-insensitive DU145 cells (note that the RASL signal for the B form in FIG. 18b is only slightly higher than background). However, quantitative RT-PCR analysis revealed that all prostate cell lines express the FGFR2 gene at the level of less than 0.01 copy per cell (data not shown).

In contrast to prostate cancer cells, a high level of KGFR expression was detected by both RASL and RT-PCR in both HT-29 (a colorectal adenocarcinoma cell line) and JAR (a choriocarcinoma cell line) cells.

We claim:

1. A method of detecting a splice junction sequence in a plurality of target pre-mRNA sequences, said method comprising:

a) hybridizing said plurality of target pre-mRNA sequences to a plurality of first splice junction specific probes and forming first hybrids wherein each of said plurality of target pre-mRNA sequences comprises a first target domain, a second target domain and a poly(A) sequence, said first target domain and said second target domain are adjacent each other and said first target domain comprises a splice junction sequence, and each of said plurality of first splice junction specific probes comprises:

i) an upstream universal priming site (UUP), wherein each of said first splice junction specific probes has the same UUP;

ii) at least one adapter; and iii) a first target-specific sequence substantially complementary to said first target domain, and said upstream universal priming site (UUP) locates in the upstream of said adapter and said first target-specific sequence;

b) hybridizing said plurality of target pre-mRNA sequences of said first hybrids to a plurality of second probes and forming second hybrids wherein each of said second hybrids comprises a said target pre-mRNA sequence, a said first splice junction specific probe and a said second probe and each of said plurality of second probes comprises:
- iv) a second target-specific sequence substantially complementary to said second target domain;
- v) a downstream universal priming site (DUP), wherein each of said second probes has the same DUP, and said downstream universal priming site (DUP) locates in the downstream of said second target-specific sequence, and wherein, in each of said plurality of first and second hybrids, said poly(A) sequence remains single-stranded;

c) contacting said second hybrids with a ligase and forming ligation complexes comprising ligated probes, each of said ligated probes comprising a said first splice junction specific probe and a said second probe;

d) contacting said ligation complexes with a support comprising a poly(T) sequence, such that said poly(A) sequence hybridizes with said poly(T) sequence;

e) removing unhybridized said first splice junction specific probes and unhybridized said second probes;

f) denaturing said ligation complexes;

g) amplifying the ligated probes using universal primers that hybridize to the UUP and DUP, or complement thereof, and generating a plurality of amplicons each comprising a said adapter;

h) contacting said amplicons with an array of capture probes to form assay complexes, wherein said capture probes bind to said adapter; and i) detecting said assay complexes wherein the detection of said assay complexes is an indication of the presence of said splice junction sequence in the pre-mRNA sequences.

2. The method according to claim 1 wherein said first target domain and said second target domain are separated by at least one base and said method further includes contacting said second hybrids with a polymerase and at least one dNTP.

3. The method according to claim 1 wherein one of said first splice junction probe and said second probes comprises a label.

4. The method according to claim 3 wherein said label is a primary label.

5. The method according to claim 4 wherein said primary label is a fluorescent label.

6. The method according to claim 1 wherein said universal primers comprise a first primer and a second primer and said amplifying in method step g) is done by:
- a) hybridizing said first universal primer to said UUP;
- b) providing a polymerase and dNTPs such that said first universal primer is extended;
- c) hybridizing said second universal primer to said DUP;
- d) providing a polymerase and dNTPs such that said second universal primer is extended; and
- e) repeating steps a) through d).

7. The method according to claim 1 wherein said capture probes comprise a first capture probe and a second capture probe and said array in method step h) comprises:
- a) a substrate with a patterned surface comprising discrete sites; and
- b) a population of microspheres comprising at least a first subpopulation comprising a said first capture probe and a second subpopulation comprising a said second capture probe.

8. The method according to claim 7 wherein said discrete sites comprises wells.

9. The method according to claim 7 wherein said substrate comprises a fiber optic bundle.

10. The method according to claim 1 wherein said support comprising a poly(T) sequence comprises magnetic beads.

11. The method according to claim 1, wherein said capture probes comprise a first capture probe and a second capture probe and said array in method step h) comprises a population of microspheres comprising at least a first subpopulation comprising a said first capture probe and a second subpopulation comprising a said second capture probe.

12. The method according to claim 11, wherein said microspheres are in a solution.

13. A method of detecting a splice junction sequence in a target pre-mRNA sequence, said method comprising:
- a) hybridizing said target pre-mRNA sequence to a first splice junction specific probe and forming a first hybrid wherein said target pre-mRNA sequence comprises a first target domain, a second target domain and a poly(A) sequence, said first target domain and said second target domain are adjacent each other and said first target domain comprises a splice junction sequence and said first splice junction specific probe comprises:
  - i) an upstream universal priming site (UUP);
  - ii) at least one adapter; and
  - iii) a first target-specific sequence substantially complementary to said first target domain, wherein said upstream universal priming site (UUP) locates in the upstream of said adapter and said first target-specific sequence, and said adapter is exogenous to said first target-specific sequence;
- b) hybridizing said target pre-mRNA sequence of said first hybrid to a sequence of a second probe and forming a second hybrid wherein said second hybrid comprises a said target pre-mRNA sequence, a said first splice junction specific probe and a said second probe and said second probe comprises:
  - iv) a second target-specific sequence substantially complementary to said second target domain;
  - v) a downstream universal priming site (DUP), wherein said downstream universal priming site (DUP) locates in the downstream of said second target-specific sequence, and said poly(A) sequence remains single-stranded in each of said first and second hybrids;
- c) contacting said second hybrid with a ligase and forming a ligation complex comprising ligated probes, each of said ligated probes comprising a said first splice junction specific probe and a said second probe;
- d) contacting said ligation complex with a support comprising a poly(T) sequence, such that said poly(A) sequence hybridizes with said poly(T) sequence;
- e) removing unhybridized said first splice junction specific probe and unhybridized said second probe;
- f) denaturing said ligation complex;
- g) amplifying the ligated probes using universal primers that hybridize to the UUP and DUP, or complement thereof, and generating a plurality of amplicons each comprising a said adapter;
- h) contacting said amplicons with an array of capture probes to form assay complexes, wherein said capture probes bind to said adapter; and
- i) detecting said assay complexes wherein the detection of said assay complexes is an indication of the presence of said splice junction sequence in the pre-mRNA sequence.

14. A method of detecting a splice junction sequence in a plurality of target pre-mRNA sequences, said method comprising:
- a) hybridizing said plurality of target pre-mRNA sequences to aplurality of first splice junction specific probes and form first hybrids wherein each of said plurality of target pre-mRNA sequences comprises a first target domain, a second target domain and a poly(A) sequence, said first target domain and said second target domain are adjacent each other and said first target domain comprises a splice junction sequence; and each of said plurality of first splice junction specific probes comprises:
  - i) an upstream universal priming site (UUP), wherein each of said first splice junction specific probes has the same UUP;
  - ii) at least one adapter; and
  - iii) a first target-specific sequence substantially complementary to said first target domain, and said upstream universal priming site (UUP) locates in the upstream of said adapter and said first target-specific sequence;
- b) hybridizing said plurality of target pre-mRNA sequences of said first hybrids to a plurality of second probes and forming second hybrids wherein each of said second hybrids comprises a said target pre-mRNA sequence, a said first splice junction specific probe and a said second probe and each of said plurality of second probes comprises:
  - iv) a second target-specific sequence substantially complementary to said second target domain;
  - v) a downstream universal priming site (DUP), wherein each of said second probes has the same DUP, and said downstream universal priming site (DUP) locates in the downstream of said second target-specific sequence;
- c) hybridizing said second hybrids to a poly(T) sequence on a solid support and forming third hybrids, such that said poly(A) sequence hybridizes with said poly(T) sequence;
- d) contacting said third hybrids with a ligase and forming ligation complexes comprising ligated probes, each of said ligated probes comprising a said first splice junction specific probe and a said second probe;
- e) removing unhybridized said first splice junction specific probes and unhybridized said second probes;
- f) denaturing said ligation complexes;
- g) amplifying the ligated probes using universal primers that hybridize to the UUP and DUP, or complement thereof, and generating a plurality of amplicons each comprising a said adapter;
- h) contacting said amplicons with an array of capture probes to form assay complexes, wherein said capture probes bind to said adapter; and
- i) detecting said assay complexes wherein the detection of said assay complexes is an indication of the presence of said splice junction sequence in the pre-mRNA sequences.

* * * * *

SEQUENCE LISTING

```
<160> NUMBER OF SEQ ID NOS: 9

<210> SEQ ID NO 1
<211> LENGTH: 20
<212> TYPE: DNA
<213> ORGANISM: unidentified adenovirus

<400> SEQUENCE: 1
caggacacag acttggactc                                                   20

<210> SEQ ID NO 2
<211> LENGTH: 20
<212> TYPE: DNA
<213> ORGANISM: Artificial sequence
<220> FEATURE:
<223> OTHER INFORMATION: synthetic

<400> SEQUENCE: 2
aaggacacag acttggactc                                                   20

<210> SEQ ID NO 3
<211> LENGTH: 20
<212> TYPE: DNA
<213> ORGANISM: Artificial sequence
<220> FEATURE:
<223> OTHER INFORMATION: synthetic

<400> SEQUENCE: 3
taggacacag acttggactc                                                   20

<210> SEQ ID NO 4
<211> LENGTH: 20
<212> TYPE: DNA
<213> ORGANISM: Artificial sequence
<220> FEATURE:
<223> OTHER INFORMATION: synthetic

<400> SEQUENCE: 4
gaggacacag acttggactc                                                   20
```

```
<210> SEQ ID NO 5
<211> LENGTH: 19
<212> TYPE: DNA
<213> ORGANISM: Artificial sequence
<220> FEATURE:
<223> OTHER INFORMATION: synthetic

<400> SEQUENCE: 5
aggacacaga cttggactc                                                 19

<210> SEQ ID NO 6
<211> LENGTH: 18
<212> TYPE: DNA
<213> ORGANISM: Artificial sequence
<220> FEATURE:
<223> OTHER INFORMATION: synthetic

<400> SEQUENCE: 6
ggacacagac ttggactc                                                  18

<210> SEQ ID NO 7
<211> LENGTH: 20
<212> TYPE: DNA
<213> ORGANISM: Artificial sequence
<220> FEATURE:
<223> OTHER INFORMATION: synthetic

<400> SEQUENCE: 7
caggacacat acttggactc                                                20

<210> SEQ ID NO 8
<211> LENGTH: 20
<212> TYPE: DNA
<213> ORGANISM: Artificial sequence
<220> FEATURE:
<223> OTHER INFORMATION: synthetic

<400> SEQUENCE: 8
caggacacat ccttggactc                                                20

<210> SEQ ID NO 9
<211> LENGTH: 20
<212> TYPE: DNA
<213> ORGANISM: Artificial sequence
<220> FEATURE:
<223> OTHER INFORMATION: synthetic

<400> SEQUENCE: 9
caggacacat cattggactc                                                20
```